(12) United States Patent
Komori

(10) Patent No.: US 6,475,955 B2
(45) Date of Patent: Nov. 5, 2002

(54) PYRIDAZINONE DERIVATIVES

(75) Inventor: Takashi Komori, Toyonaka (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/732,901

(22) Filed: Dec. 11, 2000

(65) Prior Publication Data

US 2002/0026048 A1 Feb. 28, 2002

Related U.S. Application Data

(62) Division of application No. 09/275,266, filed on Mar. 23, 1999, now Pat. No. 6,187,920.

(30) Foreign Application Priority Data

Mar. 26, 1998 (JP) .............................. 10-079031

(51) Int. Cl.[7] ..................... A01N 43/58; C07D 237/14; C07D 237/16
(52) U.S. Cl. .................. 504/238; 544/239; 544/241
(58) Field of Search ................. 544/239, 241; 504/238

(56) References Cited

U.S. PATENT DOCUMENTS

| | | | |
|---|---|---|---|
| 2,945,857 A | | 7/1960 | Hammann |
| 3,652,562 A | * | 3/1972 | Reicheneder et al. ....... 544/239 |
| 5,567,717 A | | 10/1996 | Aldous et al. |
| 5,883,090 A | | 3/1999 | Dorsch et al. |

FOREIGN PATENT DOCUMENTS

| | | |
|---|---|---|
| EP | 0711759 A1 | 5/1996 |
| EP | 0860434 A1 | 8/1998 |
| FR | 1448139 | 11/1966 |
| GB | 1073770 | 6/1967 |
| WO | 95 04461 | 2/1995 |
| WO | 9707104 | 2/1997 |
| WO | 9735845 | 10/1997 |
| WO | 9747607 | 12/1997 |
| WO | 99/18082 | * 4/1999 |

OTHER PUBLICATIONS

"Synthesis of Analogues of the 2,3,6–Triazaphenothiazine Ring System" by Charles Okafor et al., J. of Heterocyclic Chemistry vol. 20, 1983 pp. 199–203.
Hackler, et al., J. Agric. Food Chem. 38, p. 508–514 (1990).

* cited by examiner

Primary Examiner—Emily Bernhardt
(74) Attorney, Agent, or Firm—Birch, Stewart, Kolasch & Birch, LLP

(57) ABSTRACT

This invention provides pyridazinone derivatives encompassed by the following the formula:

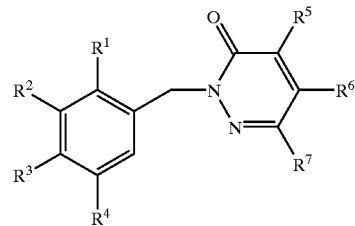

wherein, $R^1$, $R^2$, $R^3$, $R^4$, $R^5$ and $R^7$ represent a hydrogen atom and the like, and $R^6$ represents a $C_1$–$C_3$ alkyl and the like. The pyridazinone derivatives have excellent herbicidal activity, therefore, they can be used as an active ingredient for herbicidal compositions and can be utilized in herbicidal method, which are also described.

11 Claims, No Drawings

PYRIDAZINONE DERIVATIVES

This application is a divisional of Application No. 09/275,266 filed on Mar. 23, 1999, which has matured into U.S. Pat. No. 6,187,920, the entire content of which is hereby incorporated by reference.

FIELD OF THE INVENTION

The present invention relates to pyridazinone derivatives and the use of the said pyridazinone.

The object of the present invention is to provide compounds having excellent herbicidal activity.

SUMMARY OF THE INVENTION

The present inventor has intensely studied to seek out compounds that have excellent herbicidal activity, as a result, and has found that the pyridazinone derivatives encompassed by Chemical Formula 3 below, possess an excellent herbicidal activity, and arrived at the present invention. Accordingly, the present invention provides pyridazinone derivatives (hereinafter, the present invention compound) encompassed by the formula:

Chemical Formula 3

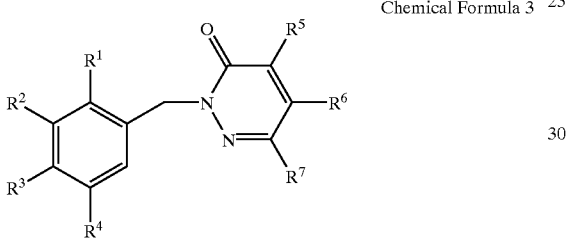

wherein, $R^1$ represents hydrogen, halogen, $C_1$–$C_3$ alkyl or $C_1$–$C_3$ haloalkyl;

$R^2$ represents hydrogen, halogen, $C_1$–$C_6$ alkyl, $C_1$–$C_6$ haloalkyl, $OR^8$, $SR^9$, $NHR^{10}$, $COOR^{11}$, $COR^{12}$, $SO_2R^{13}$, $NO_2$ or CN;

$R^3$ represents hydrogen, halogen, $C_1$–$C_6$ alkyl, $C_1$–$C_6$ haloalkyl, $C_1$–$C_3$ alkoxy $C_1$–$C_3$ alkyl, $OR^8$, $SR^9$, $NHR^{10}$, $COOR^{11}$, $COR^{12}$, $SO_2R^{13}$, $C(R^{121})$=$C(R^{14})(R^{15})$, $NO_2$ or CN;

$R^4$ represents hydrogen, halogen, $C_1$–$C_6$ alkyl, $C_1$–$C_6$ haloalkyl, $C_1$–$C_3$ alkoxy $C_1$–$C_3$ alkyl, $OR^8$, $SR^9$, $NHR^{10}$, $COOR^{11}$, $COR^{12}$, $SO_2R^{13}$, $C(R^{121})$=$C(R^{14})(R^{15})$, $C(R^{16})$=$NOR^{17}$, $NO_2$ or CN;

$R^5$ represents hydrogen, halogen or $C_1$–$C_3$ alkyl;

$R^6$ represents $C_1$–$C_3$ alkyl or $C_1$–$C_3$ haloalkyl;

$R^5$ and $R^6$ may have each end bonded to each other to form trimethylene that may be substituted with fluorine(s) or tetramethylene that may be substituted with fluorine(s);

$R^7$ represents hydrogen, halogen, or $C_1$–$C_3$ alkyl; and in which;

$R^8$ represents hydrogen, a $C_1$–$C_{10}$ alkyl, $C_1$–$C_{10}$ haloalkyl, $C_3$–$C_8$ alkenyl, $C_3$–$C_8$ haloalkenyl, $C_3$–$C_8$ alkynyl, $C_3$–$C_8$ haloalkynyl, $C_3$–$C_{10}$ cycloalkyl, $C_3$–$C_{10}$ cyclohaloalkyl, $C_3$–$C_{10}$ cycloalkenyl, $C_3$–$C_{10}$ cyclohaloalkenyl, $C_3$–$C_{10}$ cycloalkyl $C_1$–$C_3$ alkyl, $C_3$–$C_{10}$ cyclohaloalkyl $C_1$–$C_3$ alkyl, $C_3$–$C_{10}$ cycloalkenyl $C_1$–$C_3$ alkyl, $C_3$–$C_{10}$ cyclohaloalkenyl $C_1$–$C_3$ alkyl, $C_1$–$C_5$ alkylcarbonyl, $C_1$–$C_5$ haloalkylcarbonyl, $C_3$–$C_6$ cycloalkylcarbonyl, $C_3$–$C_6$ cyclohaloalkylcarbonyl, $C_1$–$C_6$ alkylcarbonyl $C_1$–$C_6$ alkyl, $C_1$–$C_6$ haloalkylcarbonyl $C_1$–$C_6$ alkyl, $C_1$–$C_6$ alkoxycarbonyl, $C_1$–$C_6$ haloalkoxycarbonyl, $C_3$–$C_{10}$ cycloalkoxycarbonyl, $C_3$–$C_{10}$ cyclohaloalkoxycarbonyl, $C_1$–$C_{10}$ alkoxycarbonyl $C_1$–$C_5$ alkyl, $C_1$–$C_{10}$ haloalkoxycarbonyl $C_1$–$C_5$ alkyl, $C_3$–$C_{10}$ cycloalkoxycarbonyl $C_1$–$C_5$ alkyl, $C_3$–$C_{10}$ cyclohaloalkoxycarbonyl $C_1$–$C_5$ alkyl, $C_1$–$C_6$ alkoxy $C_1$–$C_6$ alkyl, $C_1$–$C_6$ haloalkoxy $C_1$–$C_6$ alkyl, $C_1$–$C_6$ alkylthio $C_1$–$C_6$ alkyl, $C_1$–$C_6$ haloalkylthio $C_1$–$C_6$ alkyl, cyano $C_1$–$C_4$ alkyl, aryl that may have a substituent or substituents, aryl $C_1$–$C_3$ alkyl that may have a substituent or substituents, arylcarbonyl that may have a substituent or substituents, $SO_2R^{20}$, $CH_2C(=O)CO_2R^{41}$, $CH(CH_3)C(=O)CO_2R^{41}$, $CH_2C(=NOR^{42})CO_2R^{41}$ or $CH(CH_3)C(=NOR^{42})CO_2R^{41}$;

$R^9$ represents hydrogen, $C_1$–$C_{10}$ alkyl, $C_1$–$C_{10}$ haloalkyl, $C_3$–$C_8$ alkenyl, $C_3$–$C_8$ haloalkenyl, $C_3$–$C_8$ alkynyl, $C_3$–$C_8$ haloalkynyl, $C_3$–$C_{10}$ cycloalkyl, $C_3$–$C_{10}$ cyclohaloalkyl, $C_3$–$C_{10}$ cycloalkenyl, $C_3$–$C_{10}$ cyclohaloalkenyl, $C_3$–$C_{10}$ cycloalkyl $C_1$–$C_3$ alkyl, $C_3$–$C_{10}$ cyclohaloalkyl $C_1$–$C_3$ alkyl, $C_3$–$C_{10}$ cycloalkenyl $C_1$–$C_3$ alkyl, $C_3$–$C_{10}$ cyclohaloalkenyl $C_1$–$C_3$ alkyl, $C_1$–$C_5$ alkylcarbonyl, $C_1$–$C_5$ haloalkylcarbonyl, $C_3$–$C_6$ cycloalkylcarbonyl, $C_3$–$C_6$ cyclohaloalkylcarbonyl, $C_1$–$C_6$ alkylcarbonyl $C_1$–$C_6$ alkyl, $C_1$–$C_6$ haloalkylcarbonyl $C_1$–$C_6$ alkyl, $C_1$–$C_6$ alkoxycarbonyl, $C_1$–$C_6$ haloalkoxycarbonyl, $C_3$–$C_{10}$ cycloalkoxycarbonyl, $C_3$–$C_{10}$ cyclohaloalkoxycarbonyl, $C_1$–$C_{10}$ alkoxycarbonyl $C_1$–$C_5$ alkyl, $C_1$–$C_{10}$ haloalkoxycarbonyl $C_1$–$C_5$ alkyl, $C_3$–$C_{10}$ cycloalkoxycarbonyl $C_1$–$C_5$ alkyl, $C_3$–$C_{10}$ cyclohaloalkoxycarbonyl $C_1$–$C_5$ alkyl, $C_1$–$C_6$ alkoxy $C_1$–$C_6$ alkyl, $C_1$–$C_6$ haloalkoxy $C_1$–$C_6$ alkyl, $C_1$–$C_6$ alkylthio $C_1$–$C_6$ alkyl, $C_1$–$C_6$ haloalkylthio $C_1$–$C_6$ alkyl, cyano $C_1$–$C_4$ alkyl, aryl that may have a substituent or substituents, aryl $C_1$–$C_3$ alkyl that may have a substituent or substituents, arylcarbonyl group that may have a substituent or substituents, $CH_2C(=O)CO_2R^{41}$, $CH(CH_3)C(=O)CO_2R^{41}$, $CH_2C(=NOR^{42})CO_2R^{41}$ or $CH(CH_3)C(=NOR^{42})CO_2R^{41}$;

$R^{10}$ represents hydrogen, $C_1$–$C_{10}$ alkyl, $C_1$–$C_{10}$ haloalkyl, $C_3$–$C_8$ alkenyl, $C_3$–$C_8$ haloalkenyl, $C_3$–$C_8$ alkynyl, $C_3$–$C_8$ haloalkynyl, $C_3$–$C_{10}$ cycloalkyl, $C_3$–$C_{10}$ cyclohaloalkyl, $C_3$–$C_{10}$ cycloalkenyl, $C_3$–$C_{10}$ cyclohaloalkenyl, $C_3$–$C_{10}$ cycloalkyl $C_1$–$C_3$ alkyl, $C_3$–$C_{10}$ cyclohaloalkyl $C_1$–$C_3$ alkyl, $C_3$–$C_{10}$ cycloalkenyl $C_1$–$C_3$ alkyl, $C_3$–$C_{10}$ cyclohaloalkenyl $C_1$–$C_3$ alkyl, $C_1$–$C_5$ alkylcarbonyl, $C_1$–$C_5$ haloalkylcarbonyl, $C_3$–$C_6$ cycloalkylcarbonyl, $C_3$–$C_6$ cyclohaloalkylcarbonyl, $C_1$–$C_6$ alkylcarbonyl $C_1$–$C_6$ alkyl, $C_1$–$C_6$ haloalkylcarbonyl $C_1$–$C_6$ alkyl, $C_1$–$C_6$ alkoxycarbonyl, $C_1$–$C_6$ haloalkoxycarbonyl, $C_3$–$C_{10}$ cycloalkoxycarbonyl, $C_3$–$C_{10}$ cyclohaloalkoxycarbonyl, $C_1$–$C_{10}$ alkoxycarbonyl $C_1$–$C_5$ alkyl, $C_1$–$C_{10}$ haloalkoxycarbonyl $C_1$–$C_5$ alkyl, $C_3$–$C_{10}$ cycloalkoxycarbonyl $C_1$–$C_5$ alkyl, $C_3$–$C_{10}$ cyclohaloalkoxycarbonyl $C_1$–$C_5$ alkyl, $C_1$–$C_6$ alkoxy $C_1$–$C_6$ alkyl, $C_1$–$C_6$ haloalkoxy $C_1$–$C_6$ alkyl, $C_1$–$C_6$ alkylthio $C_1$–$C_6$ alkyl, $C_1$–$C_6$ haloalkylthio $C_1$–$C_6$ alkyl, cyano $C_1$–$C_4$ alkyl, aryl that may have a substituent or substituents, aryl $C_1$–$C_3$ alkyl that may have a substituent or substituents, arylcarbonyl that may have a substituent or substituents, $SR^{18}$, $SOR^{19}$, $SO_2R^{20}$, $CH_2C(=O)CO_2R^{41}$, $CH(CH_3)C(=O)CO_2R^{41}$, $CH_2C(=NOR^{42})CO_2R^{41}$ or $CH(CH_3)C(=NOR^{42})CO_2R^{41}$;

$R^{11}$ represents hydrogen, $C_1$–$C_{10}$ alkyl, $C_1$–$C_{10}$ haloalkyl, $C_3$–$C_{10}$ alkenyl, $C_3$–$C_{10}$ haloalkenyl, $C_3$–$C_{10}$ alkynyl, $C_3$–$C_{10}$ haloalkynyl, $C_3$–$C_8$ cycloalkyl, $C_3$–$C_8$ cycloharoalkyl, $N(R^{21})(R^{22})$, $N$=$C(R^{21})(R^{22})$, $C_1$–$C_5$ alkoxycarbonyl $C_1$–$C_3$ alkyl or $C_1$–$C_5$ haloalkoxycarbonyl $C_1$–$C_3$ alkyl;

$R^{12}$ represents hydrogen, chlorine, $C_1$–$C_5$ alkyl, $C_1$–$C_5$ haloalkyl, $C_3$–$C_6$ cycloalkyl, $C_3$–$C_6$ cyclohaloalkyl, or $N(R^{23})(R^{24})$;

$R^{13}$ represents chlorine, $C_1$–$C_{10}$ alkyl, $C_1$–$C_{10}$ haloalkyl, $N(R^{25})(R^{26})$ or $OR^{27}$;

$R^{14}$ represents hydrogen, halogen or $C_1$–$C_3$ alkyl;

$R^{15}$ represents hydrogen, $COOR^{28}$, cyano or $C_1$–$C_5$ alkyl;

$R^{16}$ represents hydrogen, $C_1$–$C_4$ alkyl, $C_1$–$C_4$ haloalkyl, $C_3$–$C_5$ cycloalkyl or $C_3$–$C_5$ cyclohaloalkyl;

$R^{17}$ represents hydrogen, $C_1$–$C_{10}$ alkyl, $C_1$–$C_{10}$ haloalkyl, $C_3$–$C_6$ cycloalkyl, $C_3$–$C_6$ cyclohaloalkyl, $C_3$–$C_{10}$ cycloalkyl $C_1$–$C_3$ alkyl, $C_3$–$C_{10}$ cyclohaloalkyl $C_1$–$C_3$ alkyl, $C_3$–$C_5$ alkenyl, $C_3$–$C_5$ haloalkenyl, $C_3$–$C_5$ alkynyl, $C_3$–$C_5$ haloalkynyl, $C_1$–$C_5$ alkoxycarbonyl $C_1$–$C_3$ alkyl, $C_1$–$C_5$ haloalkoxycarbonyl $C_1$–$C_3$ alkyl, aryl that may have a substituent or substituents or aryl $C_1$–$C_3$ alkyl that may have a substituent or substituents;

$R^{18}$ represents $C_1$–$C_{10}$ alkyl, $C_1$–$C_{10}$ haloalkyl or aryl that may have a substituent or substituents;

$R^{19}$ represents $C_1$–$C_{10}$ alkyl, $C_1$–$C_{10}$ haloalkyl, $C_3$–$C_8$ cycloalkyl, $C_3$–$C_8$ cyclohaloalkyl or aryl that may have a substituent or substituents;

$R^{20}$ represents $C_1$–$C_{10}$ alkyl, $C_1$–$C_{10}$ haloalkyl, $C_3$–$C_8$ cycloalkyl, $C_3$–$C_8$ cyclohaloalkyl or aryl that may have a substituent or substituents;

$R^{21}$ represents hydrogen or $C_1$–$C_5$ alkyl;

$R^{22}$ represents hydrogen, $C_1$–$C_5$ alkyl, $C_1$–$C_5$ haloalkyl or aryl that may have a substituent or substituents;

$R^{23}$ represents hydrogen, $C_1$–$C_{10}$ alkyl, $C_1$–$C_{10}$ haloalkyl, $C_3$–$C_{10}$ cycloalkyl, $C_3$–$C_{10}$ cyclohaloalkyl or aryl that may have a substituent or substituents;

$R^{24}$ represents hydrogen, $C_1$–$C_{10}$ alkyl or $C_1$–$C_{10}$ haloalkyl;

$R^{25}$ represents hydrogen, $C_1$–$C_5$ alkyl or $C_1$–$C_5$ haloalkyl;

$R^{26}$ represents hydrogen, $C_1$–$C_{10}$ alkyl or $C_1$–$C_{10}$ haloalkyl;

$R^{27}$ represents hydrogen, $C_1$–$C_{10}$ alkyl; and $R^{28}$ represents hydrogen, $C_1$–$C_{10}$ alkyl, $C_1$–$C_{10}$ haloalkyl, $C_3$–$C_{10}$ cycloalkyl, $C_3$–$C_{10}$ cyclohaloalkyl or aryl that may have a substituent or substituents, $R^{41}$ represents hydrogen, $C_1$–$C_6$ alkyl, $C_1$–$C_6$ haloalkyl, $C_3$–$C_8$ alkenyl and $C_3$–$C_8$ alkynyl, $R^{42}$ represents hydrogen, $C_1$–$C_6$ alkyl, $C_1$–$C_6$ haloalkyl, $C_3$–$C_8$ alkenyl and $C_3$–$C_8$ alkynyl, and $R^{121}$ represents hydrogen, chlorine, $C_1$–$C_5$ alkyl, $C_1$–$C_5$ haloalkyl, $C_3$–$C_6$ cycloalkyl or $C_3$–$C_6$ cyclohaloalkyl, and herbicides that comprise the said pyridazinone derivatives as the active ingredient.

Also, the present invention provides pyridazinone derivatives encompassed by the formula: Chemical Formula 4

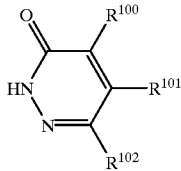

wherein, $R^{100}$ represents hydrogen, halogen or $C_1$–$C_3$ alkyl, $R^{101}$ represents $C_1$–$C_3$ haloalkyl, and $R^{102}$ represents hydrogen or $C_1$–$C_3$ alkyl, that is a productional intermediate for the production of the present invention compounds.

Furthermore, the present invention provides compounds encompassed by the formula:

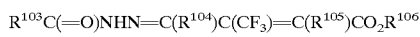

wherein $R^{103}$ represents $C_1$–$C_6$ alkyl, $C_1$–$C_6$ alkoxy or amino, $R^{104}$ represents hydrogen or $C_1$–$C_3$ alkyl, $R^{105}$ represents hydrogen or $C_1$–$C_3$ alkyl, and $R^{106}$ represents $C_1$–$C_6$ alkyl or phenyl., that is a raw material of the pyridazinone derivative given in Chemical Formula 4.

DETAILED DESCRIPTION OF THE INVENTION

In the present invention, in the definition of $R^1$, halogen means fluorine, chlorine, bromine or iodine, $C_1$–$C_3$ alkyl includes methyl, ethyl, isopropyl, etc.; and $C_1$–$C_3$ haloalkyl includes bromomethyl, chloromethyl, dichloromethyl, trichloromethyl, trifluoromethyl, pentafluoroethyl, 1,1-difluoroethyl, 3,3,3-trifluoropropyl, etc.;

in the definition of $R^2$, halogen means fluorine, chlorine, bromine or iodine atom;

$C_1$–$C_6$ alkyl includes methyl, ethyl, isopropyl, normal (hereinafter, n-) pentyl, etc.; and $C_1$–$C_6$ haloalkyl includes trichloromethyl, trifluoromethyl, chlorodifluoromethyl, pentafluoroethyl, etc.;

in the definition of $R^3$, halogen means fluorine, chlorine, bromine or iodine;

$C_1$–$C_6$ alkyl includes methyl, ethyl, isopropyl, n-butyl, etc.;

$C_1$–$C_6$ haloalkyl includes chloromethyl, dichloromethyl, trichloromethyl, trifluoromethyl, chlorodifluoromethyl, pentafluoroethyl, 1,1-difluoroethyl, 1,1-difluorohexyl, etc.; and $C_1$–$C_3$ alkoxy $C_1$–$C_3$ alkyl includes methoxymethyl, ethoxymethyl, isopropoxymethyl, methoxyethyl, etc.;

in the definition of $R^4$, halogen means fluorine, chlorine, bromine or iodine;

$C_1$–$C_6$ alkyl includes methyl, ethyl, isopropyl, n-butyl, etc.;

$C_1$–$C_6$ haloalkyl includes chloromethyl, dichloromethyl, trichloromethyl, trifluoromethyl, chlorodifluoromethyl, pentafluoroethyl, 1,1-difluoroethyl, 3,3,3-trifluoropropyl, etc.; and $C_1$–$C_3$ alkoxy $C_1$–$C_3$ alkyl includes methoxymethyl, ethoxymethyl, isopropoxymethyl, methoxyethyl, etc.;

in the definition of $R^5$, halogen atom means fluorine, chlorine, bromine or iodine; and $C_1$–$C_3$ alkyl includes methyl, ethyl, propyl or isopropyl;

in the definition of $R^6$, $C_1$–$C_3$ alkyl includes methyl, ethyl, propyl or isopropyl; and $C_1$–$C_3$ haloalkyl includes trichloromethyl, trifluoromethyl, chlorodifluoromethyl, difluoromethyl, pentafluoroethyl, 1,1-difluoroethyl, etc.;

in the definition of $R^7$, halogen atom means fluorine, chlorine, bromine or iodine atom; and $C_1$–$C_3$ alkyl includes methyl, ethyl, propyl or isopropyl;

in the definition of $R^8$, $C_1$–$C_{10}$ alkyl includes methyl, ethyl, isopropyl, n-butyl, 2-butyl, isoamyl, n-octyl, etc.;

$C_1$–$C_{10}$ haloalkyl includes trichloromethyl, trifluoromethyl, chlorodifluoromethyl, pentafluoroethyl, 2-fluoroethyl, 2,2,2-triflouroethyl, 5-chloro-n-amyl etc.;

$C_3$–$C_8$ alkenyl includes allyl, 1-methyl-2-propenyl, 3-butenyl, 2-butenyl, 3-methyl-2-butenyl, 2-methyl-3-butenyl, etc.;

$C_3$–$C_8$ haloalkenyl includes 2-chloro-2-propenyl, 3,3-dichloro-2-propenyl, etc.;

$C_3$–$C_8$ alkynyl includes propargyl, 1-methyl-2-propynyl, 2-butynyl, 3-butynyl, 1,1-dimethyl-2-propynyl, etc.;

$C_3$–$C_8$ haloalkynyl includes a 3-iodo-2-propynyl, 3-bromo-2-propynyl, etc.;

$C_3$–$C_{10}$ cycloalkyl includes cyclopropyl, cyclopentyl, cyclohexyl, etc.;

$C_3$–$C_{10}$ cyclohaloalkyl includes 2-fluorocyclopentyl, 3,4-dichlorocyclohexyl, etc., $C_3$–$C_{10}$ cycloalkenyl includes 2-cyclohexenyl, etc.;

$C_3$–$C_{10}$ cyclohaloalkenyl includes 4-chloro-2-cyclohexenyl, etc.;

$C_3$–$C_{10}$ cycloalkyl $C_1$–$C_3$ alkyl includes cyclopropylmethyl, cyclopentylmethyl, cyclohexylethyl, etc.;

$C_3$–$C_{10}$ cyclohaloalkyl $C_1$–$C_3$ alkyl includes 2-fluorocyclopentylmethyl, 3,4-dichlorocyclohexylethyl, etc.;

$C_3$–$C_{10}$ cycloalkenyl $C_1$–$C_3$ alkyl includes 2-cyclohexenylmethyl, etc.;

$C_3$–$C_{10}$ cyclohaloalkenyl $C_1$–$C_3$ alkyl includes 4-chloro-2-cyclohexenylmethyl, etc.;

$C_1$–$C_5$ alkylcarbonyl includes methylcarbonyl, ethylcarbonyl, propylcarbonyl, etc.;

$C_1$–$C_5$ haloalkylcarbonyl includes chloromethylcarbonyl, fluoromethylcarbonyl, trifluoromethylcarbonyl, dichloromethylcarbonyl, 2-chloroethylcarbonyl, etc.;

$C_3$–$C_6$ cycloalkylcarbonyl includes cyclopropylcarbonyl, etc.;

$C_3$–$C_6$ cyclohaloalkylcarbonyl includes 2-fluorocyclopentylcarbonyl, 2,2-difluorocyclopentylcarbonyl, 3,4-dichlorocyclohexylcarbonyl, etc.;

$C_1$–$C_6$ alkylcarbonyl $C_1$–$C_6$ alkyl includes methylcarbonylmethyl, ethylcarbonylmethyl, etc.;

$C_1$–$C_6$ haloalkylcarbonyl $C_1$–$C_6$ alkyl includes fluoromethylcarbonylmethyl, 2-chloroethylcarbonylmethyl, 2-fluoroethylcarbonylmethyl, 3,3,3-trifluoromethylcarbonylmethyl, etc.;

$C_1$–$C_6$ alkoxycarbonyl includes methoxycarbonyl, ethoxycabonyl, propoxycarbonyl, t-butoxycarbonyl, butoxycarbonyl, amyloxycarbonyl, isopropoxycarbonyl, isobutoxycarbonyl, isoamyloxycarbonyl, etc.;

$C_1$–$C_6$ haloalkoxycarbonyl includes chloromethyloxycarbonyl, 2-fluoroethyloxycarbonyl, 2-chloropropyloxycarbonyl, 3-chlorobutyloxycarbonyl, 2,2-dichloroethyloxycarbonyl, 2,2,2-trifluoroethyloxycarbonyl, 2,2,2-trichloroethyloxycarbonyl, etc.;

$C_3$–$C_{10}$ cycloalkoxycarbonyl includes cyclopropyloxycarbonyl, cyclobutyloxycarbonyl, cyclopentyloxycarbonyl, cyclohexyloxycarbonyl, etc.;

$C_3$–$C_{10}$ cyclohaloalkoxycarbonyl includes 2-fluorocyclopentyloxycarbonyl, 3,4-dichlorocyclohexyloxycarbonyl, etc.;

$C_1$–$C_{10}$ alkoxycarbonyl $C_1$–$C_5$ alkyl includes methoxycarbonylmethyl, ethoxycarbonylmethyl, propoxycarbonylmethyl, isopropyloxycarbonylmethyl, butoxycarbonylmethyl, isobutoxycarbonylmethyl, t-butoxycarbonylmethyl, amyloxycarbonylmethyl, isoamyloxycarbonylmethyl, t-amyloxycarbonylmethyl, 1-methoxycarbonylethyl, 1-ethoxycarbonylethyl, 1-propoxycarbonylethyl, 1-isopropoxycarbonylethyl, 1-butoxycarbonylethyl, 1-isobutoxycarbonylethyl, 1-t-butoxycarbonylethyl, 1-amyloxycarbonylethyl, 1-isoamyloxycarbonylethyl, etc.;

$C_1$–$C_{10}$ haloalkoxycarbonyl $C_1$–$C_5$ alkyl includes chloromethyloxycarbonylmethyl, 2-fluoroethyloxycarbonylmethyl, 2-chloropropyloxycarbonylmethyl, 3-chlorobutyloxycarbonylmethyl, 2,2-dichloroethyloxycarbonylmethyl, 2,2,2-trifluoroethyloxycarbonylmethyl, 2,2,2-trichloroethyloxycarbonylethyl, etc.;

$C_3$–$C_{10}$ cycloalkoxycarbonyl $C_1$–$C_5$ alkyl includes cyclopropyloxycarbonylmethyl, cyclobutyloxycarbonylmethyl, cyclopentyloxycarbonylmethyl, cyclohexyloxycarbonylmethyl, 1-cyclobutyloxycarbonylethyl, 1-cyclopentyloxycarbonylethyl, 1-cyclohexyloxycarbonylethyl, etc.;

$C_3$–$C_{10}$ cyclohaloalkoxycarbonyl $C_1$–$C_5$ alkyl includes 2-fluorocyclopentyloxycarbonylmethyl, 3,4-dichlorocyclohexyloxycarbonylethyl, etc.;

$C_1$–$C_6$ alkoxy $C_1$–$C_6$ alkyl includes methoxymethyl, 1-methoxyethyl, ethoxymethyl, etc.;

$C_1$–$C_6$ haloalkoxy $C_1$–$C_6$ alkyl includes 2,2,2-trifluoroethoxymethyl, etc.;

$C_1$–$C_6$ alkylthio $C_1$–$C_6$ alkyl includes methylthiomethyl, 1-methylthioethyl, ethylthiomethyl, etc.;

$C_1$–$C_6$ haloalkylthio $C_1$–$C_6$ alkyl includes 2,2,2-trifluoroethylthiomethyl, etc.; cyano $C_1$–$C_4$ alkyl includes cyanomethyl, etc.; aryl that may have a substituent or substituents means a phenyl, 2-chlorophenyl, 2-nitrophenyl, 2-trifluoromethylphenyl, 2-methoxyphenyl, 4-chlorophenyl, 4-nitrophenyl, 4-isopropoxyphenyl, 4-fluorophenyl, 4-trifluoromethylphenyl, 3-nitrophenyl, 3-methoxyphenyl, 3-methylphenyl, 3-trifluoromethylphenyl, 3-bromophenyl, 3-methoxycarbonylphenyl, 3-trifluoromethoxyphenyl, 3,4-dichlorophenyl, 2,4-dichlorophenyl, 2,5-dichlorophenyl, etc.;

aryl $C_1$–$C_3$ alkyl that may have a substituent or substituents means benzyl, phenethyl, 1-methylbenzyl, 2-chlorobenzyl, 3-chlorobenzyl, 4-chlorobenzyl, 2-methoxybenzyl, 3-methoxybenzyl, 4-methoxybenzyl, etc.; and arylcarbonyl that may have a substituent or substituents means benzoyl, 2-chlorobenzoyl, 3-chlorobenzoyl, 4-chlorobenzoyl, 2,3-dichlorobenzoyl, 2,4-dichlorobenzoyl, 2,5-dichlorobenzoyl, 2,6-dichlorobenzoyl, 3,4-dichlorobenzoyl, etc.;

in the definition of $R^9$, $C_1$–$C_{10}$ alkyl includes methyl, ethyl, isopropyl, n-butyl, 2-butyl, isoamyl, n-octyl, etc.;

$C_1$–$C_{10}$ haloalkyl includes trichloromethyl, trifluoromethyl, chlorodifluoromethyl, pentafluoroethyl, 2-fluoroethyl, 2,2,2-trifluoroethyl, 5-chloro-n-amyl, etc.;

$C_3$–$C_8$ alkenyl includes allyl, 1-methyl-2-propenyl, 3-butenyl, 2-butenyl, 3-methyl-2-butenyl, 2-methyl-3-butenyl, etc.;

$C_3$–$C_8$ haloalkenyl includes 2-chloro-2-propenyl, 3,3-dichloro-2-propenyl, etc.;

$C_3$–$C_8$ alkynyl includes propargyl, 1-methyl-2-propynyl, 2-butynyl, 3-butynyl, 1,1-dimethyl-2-propynyl, etc.;

$C_3$–$C_8$ haloalkynyl includes 3-iodo-2-propynyl, 3-bromo-2-propynyl, etc.;

$C_3$–$C_{10}$ cycloalkyl includes cyclopropyl, cyclopentyl, cyclohexyl, 4,4-dimethylcyclohexyl, etc.;

$C_3$–$C_{10}$ cyclohaloalkyl includes 2-fluorocyclopentyl, 3,4-dichlorocyclohexyl, etc.;

$C_3$–$C_{10}$ cycloalkenyl includes 2-cyclohexenyl, etc.;

$C_3$–$C_{10}$ cyclohaloalkenyl includes 4-chloro-2-cyclohexenyl, etc.;

$C_3$–$C_{10}$ cycloalkyl $C_1$–$C_3$ alkyl includes cyclopropylmethyl, cyclopentylmethyl, cyclohexylethyl, etc.;

$C_3$–$C_{10}$ cyclohaloalkyl $C_1$–$C_3$ alkyl includes 2-fluorocyclopentylmethyl, 3,4-dichlorocyclohexylethyl, etc.;

$C_3$–$C_{10}$ cycloalkenyl $C_1$–$C_3$ alkyl includes 2-cyclohexenylmethyl, etc.;

$C_3$–$C_{10}$ cyclohaloalkenyl $C_1$–$C_3$ alkyl includes 4-chloro-2-cyclohexenylmethyl, etc.;

$C_1$–$C_5$ alkylcarbonyl includes methylcarbonyl, ethylcarbonyl, propylcarbonyl, etc.;

$C_1$–$C_5$ haloalkylcarbonyl includes chloromethylcarbonyl, fluoromethylcarbonyl, trifluoromethylcarbonyl, dichloromethylcarbonyl, 2-chloroethylcarbonyl, etc.;

$C_3$–$C_6$ cycloalkylcarbonyl includes cyclopropylcarbonyl, etc.;

$C_3$–$C_6$ cyclohaloalkylcarbonyl includes 2-fluorocyclopentylcarbonyl, 2,2-difluorocyclopentylcarbonyl, 3,4-dichlorocyclohexylcarbonyl, etc.;

$C_1$–$C_6$ alkylcarbonyl $C_1$–$C_6$ alkyl includes methylcarbonylmethyl, ethylcarbonylmethyl, etc.;

$C_1$–$C_6$ haloalkylcarbonyl $C_1$–$C_6$ alkyl includes fluoromethylcarbonylmethyl, 2-chloroethylcarbonylmethyl, 2-fluoroethylcarbonylmethyl, 3,3,3-trifluoromethylcarbonylmethyl, etc.;

$C_1$–$C_6$ alkoxycarbonyl includes methoxycarbonyl, ethoxycabonyl, propoxycarbonyl, t-butoxycarbonyl, butoxycarbonyl, amyloxycarbonyl, isopropoxycarbonyl, isobutoxycarbonyl, isoamyloxycarbonyl, etc.;

$C_1$–$C_6$ haloalkoxycarbonyl includes chloromethyloxycarbonyl, 2-fluoroethyloxycarbonyl, 2-chloropropyloxycarbonyl, 3-chlorobutyloxycarbonyl, 2,2-dichloroethyloxycarbonyl, 2,2,2-trifluoroethyloxycarbonyl, 2,2,2-trichloroethyloxycarbonyl, etc.;

$C_3$–$C_{10}$ cycloalkoxycarbonyl includes cyclopropyloxycarbonyl, cyclobutyloxycarbonyl, cyclopentyloxycarbonyl, cyclohexyloxycarbonyl, etc.;

$C_3$–$C_{10}$ cyclohaloalkoxycarbonyl includes 2-fluorocyclopentyloxycarbonyl, 3,4-dichlorocyclohexyloxycarbonyl, etc.;

$C_1$–$C_{10}$ alkoxycarbonyl $C_1$–$C_5$ alkyl includes methoxycarbonylmethyl, ethoxycarbonylmethyl, propoxycarbonylmethyl, isopropoxycarbonylmethyl, butoxycarbonylmethyl, isobutoxycarbonylmethyl, t-butoxycarbonylmethyl, amyloxycarbonylmethyl, isoamyloxycarbonylmethyl, t-amyloxycarbonylmethyl, 1-methoxycarbonylethyl, 1-ethoxycarbonylethyl, 1-propoxycarbonylethyl, 1-isopropoxycarbonylethyl, 1-butoxycarbonylethyl, 1-isobutoxycarbonylethyl, 1-t-butoxycarbonylethyl, 1-amyloxycarbonylethyl, 1-isoamyloxycarbonylethyl, etc.;

$C_1$–$C_{10}$ haloalkoxycarbonyl $C_1$–$C_5$ alkyl includes chloromethyloxycarbonylmethyl, 2-fluoroethyloxycarbonylmethyl, 2-chloropropyloxycarbonylmethyl, 3-chlorobutyloxycarbonylmethyl, 2,2-dichloroethyloxycarbonylmethyl, 2,2,2-trifluoroethyloxycarbonylmethyl, 2,2,2-trichloroethyloxycarbonylethyl, etc.;

$C_3$–$C_{10}$ cycloalkoxycarbonyl $C_1$–$C_5$ alkyl includes cyclopropyloxycarbonylmethyl, cyclobutyloxycarbonylmethyl, cyclopentyloxycarbonylmethyl, cyclohexyloxycarbonylmethyl, 1-cyclobutyloxycarbonylethyl, 1-cyclopentyloxycarbonylethyl, 1-cyclohexyloxycarbonylethyl, etc.;

$C_3$–$C_{10}$ cyclohaloalkoxycarbonyl $C_1$–$C_5$ alkyl includes 2-fluorocyclopentyloxycarbonylmethyl, 3,4-dichlorocyclohexyloxycarbonylethyl, etc.;

$C_1$–$C_6$ alkoxy $C_1$–$C_6$ alkyl includes methoxymethyl, 1-methoxyethyl, ethoxymethyl, etc.;

$C_1$–$C_6$ haloalkoxy $C_1$–$C_6$ alkyl includes 2,2,2-trifluoroethoxymethyl, etc.;

$C_1$–$C_6$ alkylthio $C_1$–$C_6$ alkyl includes methylthiomethyl, 1-methylthioethyl, ethylthiomethyl, etc.;

$C_1$–$C_6$ haloalkylthio $C_1$–$C_6$ alkyl includes 2,2,2-trifluoroethylthiomethyl, etc.; cyano $C_1$–$C_4$ alkyl includes cyanomethyl, etc.;

aryl that may have a substituent or substituents means phenyl, 2-chlorophenyl, 2-nitrophenyl, 2-trifluoromethylphenyl, 2-methoxyphenyl, 4-chlorophenyl, 4-nitrophenyl, 4-isopropoxyphenyl, 4-fluorophenyl, 4-trifluoromethylphenyl, 3-nitrophenyl, 3-methoxyphenyl, 3-methylphenyl, 3-trifluoromethylphenyl, 3-bromophenyl, 3-methoxycarbonylphenyl, 3-trifluoromethoxyphenyl, 3,4-dichlorophenyl, 2,4-dichlorophenyl, 2,5-dichlorophenyl, etc.;

aryl $C_1$–$C_3$ alkyl that may have a substituent or substituents means benzyl, phenethyl, 1-methylbenzyl, 2-chlorobenzyl, 3-chlorobenzyl, 4-chlorobenzyl, 2-methoxybenzyl, 3-methoxybenzyl, 4-methoxybenzyl, etc.; and arylcarbonyl that may have a substituent of substituents means benzoyl, 2-chlorobenzoyl, 3-chlorobenzoyl, 4-chlorobenzoyl, 2,3-dichlorobenzoyl, 2,4-dichlorobenzoyl, 2,5-dichlorobenzoyl, 2,6-dichlorobenzoyl, 3,4-dichlorobenzoyl, etc.;

in the definition of $R^{10}$, $C_1$–$C_{10}$ alkyl includes methyl, ethyl, isopropyl, n-butyl, 2-butyl, isoamyl, n-octyl, etc.;

$C_1$–$C_{10}$ haloalkyl includes trichloromethyl, trifluoromethyl, chlorodifluoromethyl, pentafluoroethyl, 2-fluoroethyl, 2,2,2-triflouroethyl, 5-chloro-n-amyl, etc.;

$C_3$–$C_8$ alkenyl includes allyl, 1-methyl-2-propenyl, 3-butenyl, 2-butenyl, 3-methyl-2-butenyl, 2-methyl-3-butenyl, etc.;

$C_3$–$C_8$ haloalkenyl includes 2-chloro-2-propenyl, 3,3-dichloro-2-propenyl, etc.;

$C_3$–$C_8$ alkynyl includes propargyl, 1-methyl-2-propynyl, 2-butynyl, 3-butynyl, 1,1-dimethyl-2-propynyl, etc.;

$C_3$–$C_8$ haloalkynyl includes 3-iodo-2-propynyl, 3-bromo-2-propynyl, etc.;

$C_3$–$C_{10}$ cycloalkyl includes cyclopropyl, cyclopentyl, cyclohexyl, 4,4-dimethylcyclohexyl, etc.;

$C_3$–$C_{10}$ cyclohaloalkyl includes 2-fluorocyclopentyl, 3,4-dichlorocyclohexyl, etc.;

$C_3$–$C_{10}$ cycloalkenyl includes 2-cyclohexenyl, etc.;

$C_3$–$C_{10}$ cyclohaloalkenyl includes 4-chloro-2-cyclohexenyl, etc.;

$C_3$–$C_{10}$ cycloalkyl $C_1$–$C_3$ alkyl includes cyclopropylmethyl, cyclopentylmethyl, cyclohexylethyl, etc.;

$C_3$–$C_{10}$ cyclohaloalkyl $C_1$–$C_3$ alkyl includes 2-fluorocyclopentylmethyl, 3,4-dichlorocyclohexylethyl, etc.;

$C_3$–$C_{10}$ cycloalkenyl $C_1$–$C_3$ alkyl includes 2-cyclohexenylmethyl, etc.;

$C_3$–$C_{10}$ cyclohaloalkenyl $C_1$–$C_3$ alkyl includes 4-chloro-2-cyclohexenylmethyl, etc.;

$C_1$–$C_5$ alkylcarbonyl includes methylcarbonyl, ethylcarbonyl, propylcarbonyl, etc.;

$C_1$–$C_5$ haloalkylcarbonyl includes chloromethylcarbonyl, fluoromethylcarbonyl, trifluoromethylcarbonyl, dichloromethylcarbonyl, 2-chloroethylcarbonyl, etc.;

$C_3$–$C_6$ cycloalkylcarbonyl includes cyclopropylcarbonyl, etc.;

$C_3$–$C_6$ cyclohaloalkylcarbonyl includes 2-fluorocyclopentylcarbonyl, 2,2-difluorocyclopentylcarbonyl, 3,4-dichlorocyclohexylcarbonyl, etc.;

$C_1$–$C_6$ alkylcarbonyl $C_1$–$C_6$ alkyl includes methylcarbonylmethyl, ethylcarbonylmethyl, etc.;

$C_1$–$C_6$ haloalkylcarbonyl $C_1$–$C_6$ alkyl includes fluoromethylcarbonylmethyl, 2-chloroethylcarbonylmethyl, 2-fluoroethylcarbonylmethyl, 3,3,3-trifluoromethylcarbonylmethyl, etc.;

$C_1$–$C_6$ alkyloxycarbonyl includes methoxycarbonyl, ethoxycabonyl, propoxycarbonyl, t-butoxycarbonyl, butoxycarbonyl, amyloxycarbonyl, isopropoxycarbonyl, isobutoxycarbonyl, isoamyloxycarbonyl, etc.;

$C_1$–$C_6$ haloalkoxycarbonyl includes chloromethyloxycarbonyl, 2-fluoroethyloxycarbonyl, 2-chloropropyloxycarbonyl, 3-chlorobutyloxycarbonyl, 2,2-dichloroethyloxycarbonyl, 2,2,2-trifluoroethyloxycarbonyl, 2,2,2-trichloroethyloxycarbonyl, etc.;

$C_3$–$C_{10}$ cycloalkoxycarbonyl includes cyclopropyloxycarbonyl, cyclobutyloxycarbonyl, cyclopentyloxycarbonyl, cyclohexyloxycarbonyl, etc.;

$C_3$–$C_{10}$ cyclohaloalkoxycarbonyl includes 2-fluorocyclopentyloxycarbonyl, 3,4-dichlorocyclohexyloxycarbonyl, etc.;

$C_1$–$C_{10}$ alkoxycarbonyl $C_1$–$C_5$ alkyl includes methoxycarbonylmethyl, ethoxycarbonylmethyl, propoxycarbonylmethyl, isopropoxycarbonylmethyl, butoxycarbonylmethyl, isobutoxycarbonylmethyl, t-butoxycarbonylmethyl, amyloxycarbonylmethyl, isoamyloxycarbonylmethyl, t-amyloxycarbonylmethyl, 1-methoxycarbonylethyl, 1-ethoxycarbonylethyl, 1-propoxycarbonylethyl, 1-isopropoxycarbonylethyl, 1-butoxycarbonylethyl, 1-isobutoxycarbonylethyl, 1-t-butoxycarbonylethyl, 1-amyloxycarbonylethyl, 1-isoamyloxycarbonylethyl, etc.;

$C_1$–$C_{10}$ haloalkoxycarbonyl $C_1$–$C_5$ alkyl includes chloromethyloxycarbonylmethyl, 2-fluoroethyloxycarbonylmethyl, 2-chloropropyloxycarbonylmethyl, 3-chlorobutyloxycarbonylmethyl, 2,2-dichloroethyloxycarbonylmethyl, 2,2,2-trifluoroethyloxycarbonylmethyl, 2,2,2-trichloroethyloxycarbonylethyl, etc.;

$C_3$–$C_{10}$ cycloalkoxycarbonyl $C_1$–$C_5$ alkyl includes cyclopropyloxycarbonylmethyl, cyclobutyloxycarbonylmethyl, cyclopentyloxycarbonylmethyl, cyclohexyloxycarbonylmethyl, 1-cyclobutyloxycarbonylethyl, 1-cyclopentyloxycarbonylethyl, 1-cyclohexyloxycarbonylethyl, etc.;

$C_3$–$C_{10}$ cyclohaloalkoxycarbonyl $C_1$–$C_5$ alkyl includes 2-fluorocyclopentyloxycarbonylmethyl, 3,4-dichlorocyclohexyloxycarbonylethyl, etc.;

$C_1$–$C_6$ alkoxy $C_1$–$C_6$ alkyl includes a methoxymethyl, 1-methoxyethyl, ethoxymethyl, $C_1$–$C_6$ haloalkoxy $C_1$–$C_6$ alkyl includes 2,2,2-trifluoroethoxymethyl, etc.;

$C_1$–$C_6$ alkylthio $C_1$–$C_6$ alkyl includes methylthiomethyl, 1-methylthioethyl, ethylthiomethyl, etc.;

$C_1$–$C_6$ haloalkylthio $C_1$–$C_6$ alkyl includes 2,2,2-trifluoroethylthiomethyl, etc.; cyano $C_1$–$C_4$ alkyl includes cyanomethyl, etc.;

aryl that may have a substituent or substituents means phenyl, 2-chlorophenyl, 2-nitrophenyl, 2-trifluoromethylphenyl, 2-methoxyphenyl, 4-chlorophenyl, 4-nitrophenyl, 4-isopropoxyphenyl, 4-fluorophenyl, 4-trifluoromethylphenyl, 3-nitrophenyl, 3-methoxyphenyl, 3-methylphenyl, 3-trifluoromethylphenyl, 3-bromophenyl, 3-methoxycarbonylphenyl, 3-trifluoromethoxyphenyl, 3,4-dichlorophenyl, 2,4-dichlorophenyl, 2,5-dichlorophenyl, etc.;

aryl $C_1$–$C_3$ alkyl that may have a substituent or substituents means benzyl, phenethyl, 1-methylbenzyl, 2-chlorobenzyl, 3-chlorobenzyl, 4-chlorobenzyl, 2-methoxybenzyl, 3-methoxybenzyl, 4-methoxybenzyl, etc.; and arylcarbonyl that may have a substituent or substituents means benzoyl, 2-chlorobenzoyl, 3-chlorobenzoyl, 4-chlorobenzoyl, 2,3-dichlorobenzoyl, 2,4-dichlorobenzoyl, 2,5-dichlorobenzoyl, 2,6-dichlorobenzoyl, 3,4-dichlorobenzoyl, etc.;

in the definition of $R^{11}$, $C_1$–$C_{10}$ alkyl includes methyl, ethyl, isopropyl, n-butyl, t-butyl, isopentyl, n-hexyl, n-octyl, etc.;

$C_1$–$C_{10}$ haloalkyl includes 2-fluoroethyl, 2,2,2-triflouroethyl, 5-chloro-n-pentyl, 1-bromoheptyl, etc.;

$C_3$–$C_{10}$ alkenyl includes allyl, 1-methyl-2-propenyl, 3-butenyl, 2-butenyl, 3-methyl-2-butenyl, 2-methyl-3-butenyl, etc.;

$C_3$–$C_{10}$ haloalkenyl includes 2-chloro-2-propenyl, 3,3-dichloro-2-propenyl, etc.;

$C_3$–$C_{10}$ alkynyl includes propargyl, 1-methyl-2-propynyl, 2-butynyl, 3-butynyl, 1,1-dimethyl-2-propynyl, etc.;

$C_3$–$C_{10}$ haloalkynyl includes 3-iodo-2-propynyl, 3-bromo-2-propynyl, etc.;

$C_3$–$C_8$ cycloalkyl includes cyclopropyl, cyclobutyl, cyclopentyl, cyclohexyl, etc.;

$C_3$–$C_8$ cyclohaloalkyl includes 2-fluorocyclopentyl, 3,4-dichlorocyclohexyl, etc.;

$C_1$–$C_5$ alkoxycarbonyl $C_1$–$C_3$ alkyl includes methoxycarbonylmethyl, ethoxycarbonylmethyl, propoxycarbonylmethyl, isopropylcarbonylmethyl, butoxycarbonylmethyl, isobutoxycarbonylmethyl, t-butoxycarbonylmethyl, 1-methoxycarbonylethyl, 1-ethoxycarbonylethyl, 1-propoxycarbonylethyl, 1-isopropoxycarbonylethyl, 1-butoxycarbonylethyl, 1-isobutoxycarbonylethyl, 1-t-butoxycarbonylethyl, etc.;

$C_1$–$C_5$ haloalkoxycarbonyl $C_1$–$C_3$ alkyl includes chloromethyloxycarbonylmethyl, 2-fluoroethyloxycarbonylmethyl, 2-chloropropyloxycarbonylmethyl, 3-chlorobutyloxycarbonylmethyl, 1-chloro-2-propyloxycarbonylmethyl, 1,3-dichloro-2-propyloxycarbonylmethyl, 2,2-dichloroethyloxycarbonylmethyl, 2,2,2-trifluoroethyloxycarbonylmethyl, 2,2,2-trichloroethyloxycarbonylmethyl, etc.;

in the definition of $R^{12}$, $C_1$–$C_5$ alkyl includes methyl, ethyl, n-propyl, isopropyl, n-butyl, isobutyl, t-butyl, etc.;

$C_1$–$C_5$ haloalkyl includes fluoromethyl, chloromethyl, bromomethyl, trifluoromethyl, chlorodifluormethyl, difluoromethyl or pentafluoroethyl $C_3$–$C_6$ cycloalkyl includes cyclopropyl, cyclopentyl, 1-methylcyclopropyl, etc.; and $C_3$–$C_6$ cyclohaloalkyl includes 2,2-difluorocyclopropyl, 3-chlorocyclopentyl, etc.;

in the definition of $R^{13}$, $C_1$–$C_{10}$ alkyl includes methyl, ethyl, n-propyl, isopropyl, n-butyl, t-butyl, n-pentyl, n-hexyl, etc.; and $C_1$–$C_{10}$ haloalkyl includes chloromethyl, trifluoromethyl, chloroethyl, 2,2,2-trifluoroethyl, 3-chlorohexyl, etc.;

in the definition of $R^{14}$, halogen means fluorine, chlorine or bromine; and $C_1$–$C_3$ alkyl includes methyl, ethyl, propyl or isopropyl;

in the definition of $R^{15}$, $C_1$–$C_5$ alkyl includes methyl, ethyl, propyl, isopropyl, n-butyl, etc.;

in the definition of $R^{16}$, $C_1$–$C_4$ alkyl includes methyl, ethyl, isopropyl, n-butyl, etc.;

$C_1$–$C_4$ haloalkyl be a chloromethyl, 2-chloroethyl, trifluoromethyl, pentafluoroethyl, chlorodifluormethyl, etc.;

$C_3$–$C_5$ cycloalkyl includes cyclopropyl, cyclopentyl, etc.; and $C_3$–$C_5$ cyclohaloalkyl includes 2,2-difluorocyclopropyl, 3-chlorocyclopentyl, etc.;

in the definition of $R^{17}$, $C_1$–$C_{10}$ alkyl includes methyl, ethyl, n-propyl, isopropyl, n-butyl, t-butyl, n-pentyl, n-hexyl, etc.;

$C_1$–$C_{10}$ haloalkyl includes 2-chloroethyl, 2,2,2-triflouroethyl, trichloromethyl, trifluoromethyl, chlorodifluoromethyl, pentafluoroethyl, 2-fluoroethyl, 5-chloro-n-amyl, etc.;

$C_3$–$C_6$ cycloalkyl includes cyclopropyl, cyclobutyl, cyclopentyl, cyclohexyl, 1-methylcyclopropyl, etc.;

$C_3$–$C_6$ cyclohaloalkyl includes 2,2-difluorocyclopropyl, 3-chlorocyclopentyl, etc.;

$C_3$–$C_{10}$ cycloalkyl $C_1$–$C_3$ alkyl includes cyclopropylmethyl, cyclopentylmethyl, cyclohexylethyl, etc.;

$C_3$–$C_{10}$ cyclohaloalkyl $C_1$–$C_3$ alkyl includes 2-fluorocyclopentylmethyl, 3,4-dichlorocyclohexylethyl, etc.;

$C_3$–$C_5$ alkenyl includes allyl, 1-methyl-2-propenyl, 3-butenyl, 2-butenyl, 3-methyl-2-butenyl, 2-methyl-3-butenyl, etc.;

$C_3$–$C_5$ haloalkenyl includes 2-chloro-2-propenyl, 3,3-dichloro-2-propenyl, etc.;

$C_3$–$C_5$ alkynyl includes propargyl, 1-methyl-2-propynyl, 2-butynyl, 3-butynyl, 1,1-dimethyl-2-propynyl, etc.;

$C_3$–$C_5$ haloalkynyl includes 3-iodo-2-propynyl, 3-bromo-2-propynyl, etc.;

$C_1$–$C_5$ alkoxycarbonyl $C_1$–$C_3$ alkyl includes methoxycarbonylmethyl, ethoxycabonylmethyl, propoxycarbonylmethyl, isopropoxycarbonylmethyl, butoxycarbonylmethyl, isobutoxycarbonylmethyl, t-butoxycarbonylmethyl, 1-methoxycarbonylethyl, 1-ethoxycarbonylethyl, 1-propoxycarbonylethyl, 1-isopropoxycarbonylethyl, 1-butoxycarbonylethyl, 1-isobutoxycarbonylethyl, 1-t-butoxycarbonylethyl, etc.;

$C_1$–$C_5$ haloalkoxycarbonyl $C_1$–$C_3$ alkyl includes chloromethyloxycarbonylmethyl, 2-fluoroethyloxycarbonylmethyl, 2-chloropropyloxycarbonylmethyl, 3-chlorobutyloxycarbonylmethyl, 2,2-dichloroethyloxycarbonylmethyl, 2,2,2-trifluoroethyloxycarbonylmethyl, 2,2,2-trichloroethyloxycarbonylethyl, etc.;

aryl that may have a substituent or substituents means phenyl, 2-chlorophenyl, 2-nitrophenyl, 2-trifluoromethylphenyl, 2-methoxyphenyl, 4-chlorophenyl, 4-nitrophenyl, 4-isopropoxyphenyl, 4-fluorophenyl, 4-trifluoromethylphenyl, 3-nitrophenyl, 3-methoxyphenyl, 3-methylphenyl, 3-trifluoromethylphenyl, 3-bromophenyl, 3-methoxycarbonylphenyl, 3-trifluoromethoxyphenyl, 3,4-dichlorophenyl, 2,4-dichlorophenyl, 2,5-dichlorophenyl, etc.;

aryl $C_1$–$C_3$ alkyl that may have a substituent or substituents means benzyl, phenethyl, 1-methylbenzyl, 2-chlorobenzyl, 3-chlorobenzyl, 4-chlorobenzyl, 2-methoxybenzyl, 3-methoxybenzyl, 4-methoxybenzyl, etc.;

in the definition of $R^{18}$, $C_1$–$C_{10}$ alkyl includes methyl, ethyl, isopropyl, n-butyl, isopentyl, n-octyl, etc.;

$C_1$–$C_{10}$ haloalkyl includes 2-fluoroethyl, 2,2,2-triflouroethyl, 5-chloro-n-pentyl, etc.; and aryl that may have a substituent or substituents means a phenyl, 2-chlorophenyl, 2-nitrophenyl, 2-trifluoromethylphenyl, 2-methoxyphenyl, 4-chlorophenyl, 4-nitrophenyl, 4-isopropoxyphenyl, 4-fluorophenyl, 4-methylphenyl, 4-trifluoromethylphenyl, 3-nitrophenyl, 3-methoxyphenyl, 3-methylphenyl, 3-trifluoromethylphenyl, 3-bromophenyl, 3-methoxycarbonylphenyl, 3-trifluoromethoxyphenyl, 3,4-dichlorophenyl, 2,4-dichlorophenyl, 2,5-dichlorophenyl, etc.;

in the definition of $R^{19}$, $C_1$–$C_{10}$ alkyl includes methyl, ethyl, isopropyl, n-butyl, isopentyl, n-octyl, etc.;

$C_1$–$C_{10}$ haloalkyl includes 2-fluoroethyl, 2,2,2-triflouroethyl, 5-chloro-n-pentyl, etc.;

$C_3$–$C_8$ cycloalkyl includes cyclopropyl, cyclopentyl, cyclohexyl, etc.;

$C_3$–$C_8$ cyclohaloalkyl includes 2-fluorocyclopentyl, 3,4-dichlorocyclohexyl, etc.; and aryl that may have a substituent or substituents means phenyl, 2-chlorophenyl, 2-nitrophenyl, 2-trifluoromethylphenyl, 2-methoxyphenyl, 4-chlorophenyl, 4-nitrophenyl, 4-isopropoxyphenyl, 4-fluorophenyl, 4-methylphenyl, 4-trifluoromethylphenyl, 3-nitrophenyl, 3-methoxyphenyl, 3-methylphenyl, 3-trifluoromethylphenyl, 3-bromophenyl, 3-methoxycarbonylphenyl, 3-trifluoromethoxyphenyl, 3,4-dichlorophenyl, 2,4-dichlorophenyl, 2,5-dichlorophenyl, etc.;

in the definition of $R^{20}$, $C_1$–$C_{10}$ alkyl includes methyl, ethyl, isopropyl, n-butyl, isopentyl, n-octyl, etc.;

$C_1$–$C_{10}$ haloalkyl includes chloromethyl, trichloromethyl, trifluoromethyl, 2-chloroethyl, 2-fluoroethyl, 3-chloropropyl, 2,2,2-trifluoroethyl, 5-chloro-n-pentyl, etc.;

$C_3$–$C_8$ cycloalkyl includes cyclopropyl, cyclobutyl, cyclopentyl, cyclohexyl, etc.;

$C_3$–$C_8$ cyclohaloalkyl includes 2,2-difluorocyclopropyl, 3-chlorocyclopentyl, 4,4-difluorocyclohexyl, etc.; and aryl that may have a substituent or substituents means phenyl, 2-chlorophenyl, 2-nitrophenyl, 2-trifluoromethylphenyl, 2-methoxyphenyl, 4-chlorophenyl, 4-nitrophenyl, 4-isopropoxyphenyl, 4-fluorophenyl, 4-methylphenyl, 4-trifluoromethylphenyl, 3-nitrophenyl, 3-methoxyphenyl, 3-methylphenyl, 3-trifluoromethylphenyl, 3-bromophenyl, 3-methoxycarbonylphenyl, 3-trifluoromethoxyphenyl, 3,4-dichlorophenyl, 2,4-dichlorophenyl, 2,5-dichlorophenyl, etc.;

in the definition of $R^{21}$, $C_1$–$C_5$ alkyl includes methyl, ethyl, n-propyl, isopropyl, butyl, etc.;

in the definition of $R^{22}$, $C_1$–$C_5$ alkyl includes methyl, ethyl, n-propyl, isopropyl, butyl, etc.;

$C_1$–$C_5$ haloalkyl includes 2-chloroethyl, 2-fluoroethyl, 3-chloro-n-propyl, 2-chloro-2-methylpropyl, etc.; and aryl that may have a substituent or substituents means phenyl, 2-chlorophenyl, 2-nitrophenyl, 2-trifluoromethylphenyl, 2-methoxyphenyl, 4-chlorophenyl, 4-nitrophenyl, 4-isopropoxyphenyl, 4-fluorophenyl, 4-methylphenyl, 4-trifluoromethylphenyl, 3-nitrophenyl, 3-methoxyphenyl, 3-methylphenyl, 3-trifluoromethylphenyl, 3-bromophenyl, 3-methoxycarbonylphenyl, 3-trifluoromethoxyphenyl, 3,4-dichlorophenyl, 2,4-dichlorophenyl or 2,5-dichlorophenyl, 3,4-dimethylphenyl, 2,4-dimethylphenyl, 2,5-dimethylphenyl, etc.;

in the definition of $R^{23}$, $C_1$–$C_{10}$ alkyl includes methyl, ethyl, isopropyl, n-butyl, isopentyl, n-octyl, 4,4-dimethyl-n-hexyl, etc.;

$C_1$–$C_{10}$ haloalkyl includes 2-fluoroethyl, 2-chloroethyl, 3-chloro-n-propyl, 2,2,2-trifluoroethyl, 5-chloro-n-pentyl, 1-bromoheptyl, etc.;

$C_3$–$C_{10}$ cycloalkyl includes cyclopropyl, cyclobutyl, cyclopentyl, cyclohexyl, etc.;

$C_3$–$C_{10}$ cyclohaloalkyl includes 2,2-difluorocyclopropyl, 3-chlorocyclopentyl, 4,4-difluorocyclohexyl, etc.; and aryl that may have a substituent or substituents means phenyl, 2-chlorophenyl, 2-nitrophenyl, 2-trifluoromethylphenyl, 2-methoxyphenyl, 4-chlorophenyl, 4-nitrophenyl, 4-isopropoxyphenyl, 4-fluorophenyl, 4-methylphenyl, 4-trifluoromethylphenyl, 3-nitrophenyl, 3-methoxyphenyl, 3-methylphenyl, 3-trifluoromethylphenyl, 3-bromophenyl, 3-methoxycarbonylphenyl, 3-trifluoromethoxyphenyl, 3,4-dichlorophenyl, 2,4-dichlorophenyl, 2,5-dichlorophenyl, 3,4-dimethylphenyl, 2,4-dimethylphenyl, 2,5 dimethylphenyl, etc.;

in the definition of $R^{24}$, $C_1$–$C_{10}$ alkyl includes methyl, ethyl, isopropyl, n-butyl, t-butyl, n-pentyl, isopentyl, n-octyl, 4,4-dimethyl-n-hexyl, etc.; and $C_1$–$C_{10}$ haloalkyl includes 2-fluoroethyl, 2-chloroethyl, 3-chloro-n-propyl, 2,2,2-trifluoroethyl, 5-chloro-n-pentyl, 1-bromoheptyl, etc.;

in the definition of $R^{25}$, $C_1$–$C_5$ alkyl includes methyl, ethyl, isopropyl, n-butyl, t-butyl, n-pentyl, isopentyl, etc.; and $C_1$–$C_5$ haloalkyl includes 2-fluoroethyl, 2-chloroethyl, 3-chloro-n-propyl, 2,2,2-trifluoroethyl, 5-chloro-n-pentyl, etc.;

in the definition of $R^{26}$, $C_1$–$C_{10}$ alkyl includes methyl, ethyl, isopropyl, n-butyl, t-butyl, n-pentyl, isopentyl, n-octyl, 4,4-dimethyl-n-hexyl, etc.; and $C_1$–$C_{10}$ haloalkyl includes 2-fluoroethyl, 2-chloroethyl, 3-chloro-n-propyl, 2,2,2-trifluoroethyl, 5-chloro-n-pentyl, 2-chloro-1,1,4,4-tetramethylhexyl, etc.;

in the definition of $R^{27}$, $C_1$–$C_{10}$ alkyl includes methyl, ethyl, propyl, isopropyl, n-butyl, isobutyl, t-butyl, n-pentyl, isopentyl, n-hexyl, n-octyl, etc.;

in the definition of $R^{28}$, $C_1$–$C_{10}$ alkyl includes methyl, ethyl, propyl, isopropyl, n-butyl, isobutyl, t-butyl, n-pentyl, isopentyl, n-hexyl, n-octyl, etc.;

$C_1$–$C_{10}$ haloalkyl includes 2-fluoroethyl, 2-chloroethyl, 3-chloro-n-propyl, 2,2,2-trifluoroethyl, 5-chloro-n-pentyl, etc.

$C_3$–$C_{10}$ cycloalkyl includes cyclopropyl, cyclopentyl, cyclohexyl, etc.;

$C_3$–$C_{10}$ cyclohaloalkyl includes 2,2-difluorocyclopropyl, 3-chlorocyclopentyl, 4,4-difluorocyclohexyl, etc.; and aryl that may have a substituent or substituents means phenyl, 2-chlorophenyl, 2-nitrophenyl, 2-trifluoromethylphenyl, 2-methoxyphenyl, 4-chlorophenyl, 4-nitrophenyl, 4-isopropoxyphenyl, 4-fluorophenyl, 4-methylphenyl, 4-trifluoromethylphenyl, 3-nitrophenyl, 3-methoxyphenyl, 3-methylphenyl, 3-trifluoromethylphenyl, 3-bromophenyl, 3-methoxycarbonylphenyl, 3-trifluoromethoxyphenyl, 3,4-dichlorophenyl, 2,4-dichlorophenyl, 2,5- dichlorophenyl, 3,4-dimethylphenyl, 2,4-dimethylphenyl, 2,5 dimethylphenyl, etc.;
in the definition of $R^{41}$, $C_1$–$C_6$ alkyl includes methyl, ethyl, propyl, isopropyl, n-butyl, t-butyl, etc.;

$C_1$–$C_6$ haloalkyl includes chloromethyl, bromomethyl, trichloromethyl, trifluoromethyl, 2-fluoroethyl, 2-chloroethyl, 2,2,2-trifluoroethyl, etc.;

$C_3$–$C_8$ alkenyl includes allyl, 1-methyl-2-propenyl, 3-butenyl, 2-butenyl, 3-methyl-2-butenyl, 2-methyl-3-butenyl, etc.; and $C_3$–$C_8$ alkynyl includes propargyl, 1-methyl-2-propynyl, 2-butynyl, 3-butynyl, 1,1-dimethyl-2-propynyl, etc.;
in the definition of $R^{42}$, $C_1$–$C_6$ alkyl includes methyl, ethyl, propyl, isopropyl, n-butyl, t-butyl, etc.;

$C_1$–$C_6$ haloalkyl includes chloromethyl, bromomethyl, trichloromethyl, trifluoromethyl, 2-fluoroethyl, 2-chloroethyl, 2,2,2-trifluoroethyl, etc.;

$C_3$–$C_8$ alkenyl includes allyl, 1-methyl-2-propenyl, 3-butenyl, 2-butenyl, 3-methyl-2-butenyl, 2-methyl-3-butenyl, etc.; and $C_3$–$C_8$ alkynyl includes propargyl, 1-methyl-2-propynyl, 2-butynyl, 3-butynyl, 1,1-dimethyl-2-propynyl, etc.;
in the definition of $R^{121}$, $C_1$–$C_5$ alkyl includes methyl, ethyl, isopropyl, n-butyl, t-butyl, n-pentyl, isopentyl, etc.;

$C_1$–$C_5$ haloalkyl includes 2-fluoroethyl, 2-chloroethyl, 3-chloro-n-propyl, 2,2,2-trifluoroethyl, 5-chloro-n-pentyl, etc.;

$C_3$–$C_6$ cycloalkyl includes cyclopropyl, cyclobutyl, cyclopentyl, cyclohexyl, etc.; and $C_3$–$C_6$ cyclohaloalkyl includes 2,2-difluorocyclopropyl, 3-chlorocyclopentyl, 4,4-difluorocyclohexyl, etc.;
in the definition of $R^{100}$, halogen atom means fluorine, chlorine, bromine or iodine, and $C_1$–$C_3$ alkyl includes methyl, ethyl, propyl, isopropyl;
in the definition of $R^{101}$, $C_1$–$C_3$ haloalkyl includes trichloromethyl, trifluoromethyl, difluoromethyl, chlorodifluoromethyl, pentafluoroethyl, 1,1-difluoroethyl, etc.;
in the definition of $R^{102}$, $C_1$–$C_3$ alkyl includes methyl, ethyl, propyl, isopropyl;
in the definition of $R^{103}$, $C_1$–$C_6$ alkyl includes methyl, ethyl, t-butyl, etc.; and $C_1$–$C_6$ alkoxy includes methoxy, ethoxy, t-butoxy, etc.;
in the definition of $R^{104}$, $C_1$–$C_3$ alkyl includes methyl, ethyl, propyl or isopropyl;
in the definition of $R^{105}$, $C_1$–$C_3$ alkyl includes methyl, ethyl, propyl or isopropyl; and
in the definition of $R^{106}$, $C_1$–$C_6$ alkyl includes methyl, ethyl, etc..

Among the present invention compounds, preferred are
2-(2,3,5-trichlorobenzyl)-5-(trifluoromethyl)-2,3-dihydropyridazin-3-one,
2-(2,3,5-trichlorobenzyl)-4-methyl-5-(trifluoromethyl)-2,3-dihydropyridazin-3-one,
2-(2,3,5-trichlorobenzyl)-5-(chlorodifluoromethyl)-2,3-dihydropyridazin-3-one,
2-(2,3,5-trichlorobenzyl)-4-methyl-5-(chlorodifluoromethyl)-2,3-dihydropyridazin-3-one,
2-(2,3,5-trichlorobenzyl)5-(1,1-difluoroethyl)-2,3-dihydropyridazin-3-one, and
2-(2,3,5-trichlorobenzyl)-4-methyl-5 -(1,1-difluoroethyl)-2,3-dihydropyridazin-3-one.

Moreover, for the present compound invention, there are situations when double bonds educe geometric isomers or when asymmetric carbons educe optical isomers and diastereoisomers. As such, the present invention compounds may also contain isomers thereof and mixture of such isomers.

The present invention compound, for example, may be produced by utilizing the following production method 1 and production method 2.

(production method 1)

A method which comprises reacting the pyridazinone derivative having the following formula:

Chemical Formula 5 wherein, $R^5$, $R^6$ and $R^7$ have the same definition as mentioned above, with the benzyl derivative having the following formula:

Chemical Formula 6 wherein, $R^1$, $R^2$, $R^3$ and $R^4$ have the same definition as mentioned above, and X represents chlorine, bromine, methanesulfonyloxy or p-toluenesulfonyloxy, in the presence of a base.

The said reaction is usually performed without any solvent or in a solvent. The limits to the reaction temperature are from 0 to 200° C., and the limits to the reaction time are usually from a moment to 24 hours.

For the amount of the agents used in the reaction, based on 1 mole of the pyridazinone derivative of Chemical Formula 5, a ratio of 1 mole of the benzyl derivative of Chemical Formula 6 and a rate of 1 mole of the base are the theoretical amounts, but may be optionally altered to correspond to the condition of the reaction.

As the base, organic bases such as pyridine, 4-dimethylaminopyridine, N,N-dimethylaniline, N,N-diethylaniline, triethylamine and diisopropylethylamine, and inorganic bases such as sodium carbonate, potassium carbonate, sodium hydride, potassium hydride, sodium hydroxide and potassium hydroxide may be set forth.

As the solvent, aliphatic hydrocarbons such as hexane, heptane, octane and ligroin; aromatic hydrocarbons such as benzene, toluene, ethylbenzene, xylene and mesitylene; ethers such as 1,4-dioxane, tetrahydrofuran, ethylene glycol dimethyl ether and methyl-t-butyl ether; nitro compounds such as nitrobenzene; acid amides such as N,N-dimethylformamide; sulfur compounds such as dimethylsulfoxide (hereinafter, written as DMSO) and sulfolane; or a mixture thereof may be set forth.

After the completion of the reaction, the reaction mixture is subjected to the ordinary post-treatment such as pouring into water, extracting with an organic solvent, drying the organic layer and concentrating it. If necessary, purification such as recrystallization or column chromatography may be carried out. Thus the present invention compound can be obtained.

(production method 2)

A production method that complies to the following scheme:

Chemical Formula 7

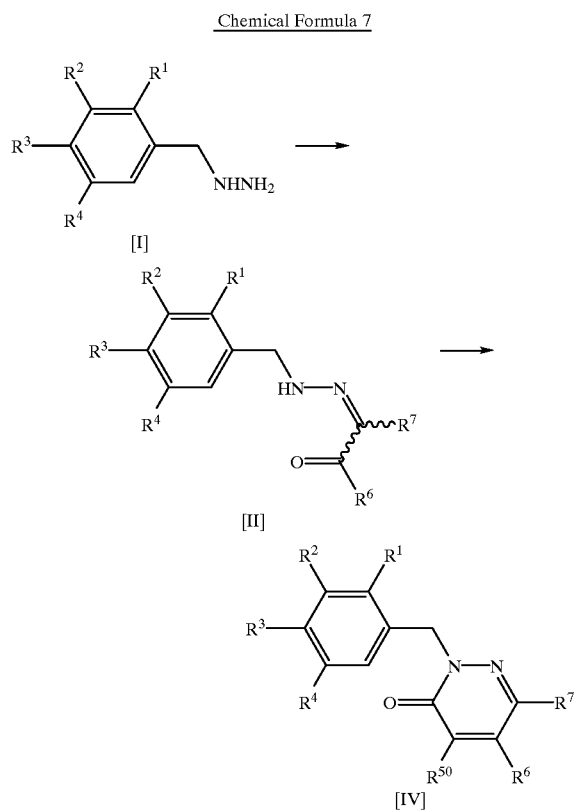

wherein, $R^{50}$ represents hydrogen or $C_1$–$C_3$ alkyl and $R^1$, $R^2$, $R^3$, $R^4$, $R^6$ and $R^7$ have the same definition as mentioned above.

The reaction of each step may be, for example, performed by corresponding to the methods reported in International Patent Publication WO 97/07104 publication, or for example performed according to the following methods.

1) A method to produce compound [II] from compound [I]

Compound [II] may be produced by previously reacting the α-dihalo compound having the formula $R^6C(=O)CV_2R^7$ wherein, $R^6$ and $R^7$ have the same definition as mentioned above, and V represents iodine, bromine or chlorine, with water in the presence of a base, to obtain the carbonyl derivative having the formula $R^6C(=O)C(=O)R^7$ wherein, $R^6$ and $R^7$ have the same definition as mentioned above, (hereinafter, Reaction 1), and subsequently, reacting with compound [I] (hereinafter, Reaction 2). The carbonyl derivative having the formula $R^6C(=O)C(=O)R^7$ wherein, $R^6$ and $R^7$ have the same definition as mentioned above, may also be reacted in water or alcohol as a hydrate or acetal derivative.

Reaction 1 is usually performed within a solvent. The limits to the reaction temperature are usually from 20 to 100° C., and the limits to the reaction time are usually from a moment to 24 hours. For the amounts of the agents used in the reaction, based on 1 mole of α-dihalo compound having the formula ($R^6C(=O)CV_2R^7$), a rate of 2 moles is the theoretical amount of each water and the base, but may be optionally altered to correspond to the condition of the reaction.

As the base, organic bases and inorganic bases both may be utilized, and for example, sodium acetate and potassium acetate may be set forth.

As the solvent, aliphatic hydrocarbons such as hexane, heptane, ligroin, cyclohexane and petroleum ether; aromatic hydrocarbons such as benzene, toluene and xylene; halogenated hydrocarbons such as chlorobenzene and dichlorobenzene, ethers such as diethyl ethers, diisopropyl ether, dioxane, THF and ethylene glycol dimethyl ether; esters such as ethyl formate, ethyl acetate, butyl acetate and diethyl carbonate; nitro compounds such as nitromethane and nitrobenzene; nitriles such as acetonitrile and isobutylonitrile; acid amides such as DMF; tertiary amines such as pyridine, triethylamine, diisopropylethylamine, N,N-dimethylaniline, N,N-diethylaniline and N-methylmorpholine; sulfur compounds such as DMSO and sulfolane; alcohols such as methanol, ethanol, ethylene glycol, isopropanol and t-butanol; or water a mixture thereof may be set forth.

Reaction 2 is usually performed within a solvent. The limits to the reaction temperature are usually from –20 to 200° C., and the limits to the reaction time are usually from a moment to 72 hours. For the amounts of the agents used in the reaction, based on 1 mole of α-dihalo compound utilized in Reaction 1, a rate of 1 mole is the theoretical amount of compound [I], but may be optionally altered to correspond to the condition of the reaction. Furthermore, the salt of compound [I] (for example, hydrochloric acid salt or sulfuric acid salt) may be utilized to correspond with the condition of the reaction.

As the solvent, aliphatic hydrocarbons such as hexane, heptane, ligroin, cyclohexane and petroleum ether; aromatic hydrocarbons such as benzene, toluene and xylene; halogenated hydrocarbons such as chloroform, carbon tetrachloride, dichloromethane, dichloroethane, chlorobenzene and dichlorobenzene; ethers such as diethyl ether, diisopropyl ether, dioxane, THF and ethylene glycol dimethyl ether; esters such as ethyl formate, ethyl acetate, butyl acetate and diethyl carbonate; nitro compounds such as nitromethane and nitrobenzene; nitriles such as acetonitrile and isobutylonitrile; acid amides such as formamide, DMF and acetamide; tertiary amines such as pyridine, triethylamine, diisopropylethylamine, N,N-dimethylaniline, N,N-diethylaniline and N-methylmorpholine; sulfur compounds such as DMSO and sulfolane; fatty acids such as formic acid, acetic acid and propionic acid; alcohols such as methanol, ethanol, ethylene glycol, isopropanol and t-butanol; water; or a mixture thereof are set forth.

After the completion of the reaction, the precipitated crystals may be collected by filtration or the reaction mixture may be subjected to the ordinary post-treatment such as extraction with an organic solvent and concentration. If necessary, a purification procedure such as chromatography and recrystallization may be conducted. Thus the objective material may be isolated.

2) A method to produce compound [IV] from compound [II]

Compound [IV] may be produced by reacting compound [II] and the phosphorane compound having the formula

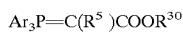

$$Ar_3P=C(R^5)COOR^{30}$$

wherein, $R^{50}$ has the same definition as mentioned above, $R^{30}$ represents $C_1$–$C_6$ alkyl such as methyl or ethyl, Ar represents a phenyl that may have substituent(s) such as phenyl..

The said reaction is usually performed within a solvent. The limits to the reaction temperature are usually from −20 to 150° C., preferably from 0 to 100° C., and the limits to the reaction time are usually from a moment to 72 hours. For the amounts of the agents used in the reaction, based on 1 mole of compound [II], a rate of 1 mole is the theoretical amount of phosphorane, but may be optionally altered to correspond to the condition of the reaction.

As solvents that may be utilized, aliphatic hydrocarbons such as hexane, heptane, ligroin, cyclohexane and petroleum ether; aromatic hydrocarbons such as benzene, toluene and xylene; ethers such as diethyl ether, diisopropyl ether, dioxane, THF and ethylene glycol dimethyl ether; nitro compounds such as nitromethane and nitrobenzene; acid amides such as formamide, DMF and acetamide; tertiary amines such as pyridine, triethylamine, diisopropylethylamine, N,N-dimethylaniline, N,N-diethylaniline and N-methylmorpholine; sulfur compounds such as DMSO and sulfolane; alcohols such as methanol, ethanol, ethylene glycol, isopropanol and t-butanol; water; or a mixture thereof are set forth.

After the completion of the reaction, the reaction mixture may be subjected to distillation to remove the reaction solvent and then the residue may be subjected to chromatography, or the reaction mixture may be subjected to the ordinary post-treatment such as extraction with an organic solvent and concentration. If necessary, further purification such as chromatography and recrystallization may be conducted. Thus the objective material can be isolated.

(production method 3)

A production method that complies to the following scheme:

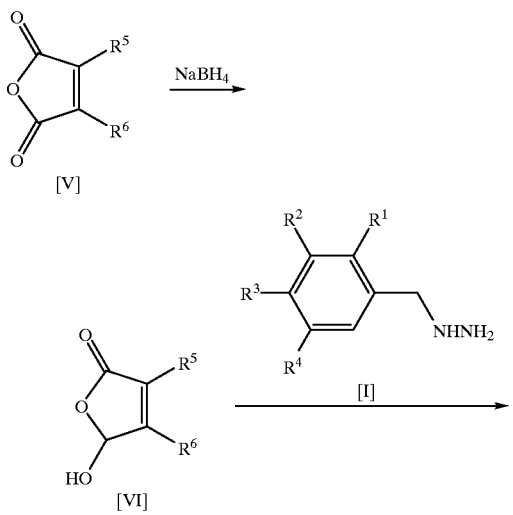

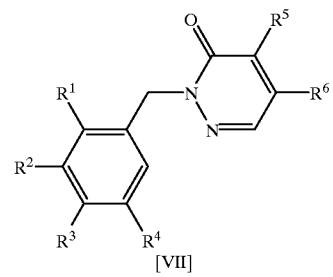

wherein $R^1$, $R^2$, $R^3$, $R^4$, $R^5$ and $R^6$ have the same definition as mentioned above.

1) A method to produce compound [VI] from compound [V]

Compound [VI] may be produced by reacting compound [V] with sodium boron hydride.

The reaction is usually performed within a solvent. The limits to the reaction temperature are usually from −10 to 50° C., and the limits to the reaction time are usually from a moment to 12 hours. For the amounts of the agents used in the reaction, based on 1 mole compound [V], a rate of 0.25 mole is the theoretical amount of sodium boron hydride, but may be optionally altered to correspond to the condition of the reaction.

As the solvent, ethers such as dioxane and THF, alcohols such as methanol and ethanol, or a mixture thereof may be set forth.

After the completion of the reaction, the reaction mixture may be poured into water and subjected to the ordinary post-treatment such as extraction with an organic solvent and concentration. If necessary, further purification procedure such as chromatography and recrystallization may be conducted. Thus the objective material may be isolated.

2) A method to produce compound [VII] from compound [VI]

Compound [VII] may be produced by reacting compound [VI] with compound [I].

The reaction is usually performed within a solvent. The limits to the reaction temperature are usually from 50 to 120° C., and the limits to the reaction time are usually from a moment to 72 hours. For the amounts of the agents used in the reaction, based on 1 mole compound [VI], a rate of 1 mole is the theoretical amount of compound [I], but may be optionally altered to correspond to the condition of the reaction.

As the solvent, organic acids such as acetic acid and propionic acid may be set forth.

After the completion of the reaction, the reaction mixture may be poured into water to correct the precipitated crystals or may be subjected to the ordinary post-treatment such as extraction with an organic solvent and concentration. If necessary, further purification procedure such as chromatography and recrystallization may be conducted. Thus the objective material may be isolated.

Hereinafter, the production methods of the intermediates or raw materials used when producing the present invention compounds are set forth.

The pyridazinone derivative of Chemical Formula 5 which is the raw material utilized when producing the present invention compounds by production method 1 may be produced, for example, according to the following production method 4 or 5.

(production method 4)

A production method according to the following scheme given in Chemical Formula 8:

Chemical Formula 8

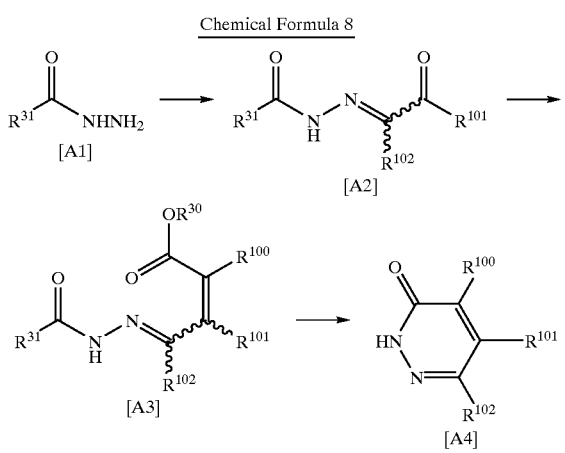

wherein, $R^{100}$, $R^{101}$, $R^{102}$ and $R^{30}$ have the same definition as mentioned above, and $R^{31}$ represents amino, $C_1$–$C_6$ alkyl such as methyl, ethyl and t-butyl, or $C_1$–$C_6$ alkoxy such as methoxy, ethoxy and t-butoxy.

The reaction conditions for each procedure are given, for example, below.

1) A method to produce compound [A2] from compound [A1]

Compound [A2] may be produced by previously reacting the α-dihalo compound having the formula $$R^{101}C(=O)CV_2R^{102}$$

wherein, $R^{101}$, $R^{102}$ and V have the same definition as mentioned above with water in the presence of a base to obtain the carbonyl derivative having the formula $$R^{101}C(=O)C(=O)R^{102}$$

wherein, $R^{101}$ and $R^{102}$ have the same definition as mentioned above (reaction 1), and subsequently, reacting with compound [A1] (reaction 2). The carbonyl derivative having the formula $$R^{101}C(=O)C(=O)R^{102}$$

wherein, $R^{101}$ and $R^{102}$ have the same definition as mentioned above may also be reacted in water or alcohol, and as a hydrate or acetal derivative.

Reaction 1 is usually performed within a solvent. The limits to the reaction temperature are usually from 20 to 100° C., and the limits to the reaction time are usually from a moment to 24 hours. For the amounts of the agents used in the reaction, based on 1 mole of α-dihalo compound $R^{101}C(=O)CV_2R^{102}$, a rate of 2 moles is the theoretical amount of each water and the base, but may be optionally altered to correspond to the condition of the reaction.

As the base that may be used, organic bases and inorganic bases both may be utilized, and for example, sodium acetate, potassium acetate and the like may be set forth.

As the solvent, aliphatic hydrocarbons such as hexane, heptane, ligroin, cyclohexane and petroleum ether; aromatic hydrocarbons such as benzene, toluene and xylene; halogenated hydrocarbons such as chlorobenzene and dichlorobenzene; ethers such as diethyl ethers, diisopropyl ether, dioxane, THF and ethylene glycol dimethyl ether; esters such as ethyl formate, ethyl acetate, butyl acetate and diethyl carbonate; nitro compounds such as nitromethane and nitrobenzene; nitriles such as acetonitrile and isobutylonitrile; acid amides such as DMF; tertiary amines such as pyridine, triethylamine, diisopropylethylamine, N,N-dimethylaniline, N,N-diethylaniline and N-methylmorpholine; sulfur compounds such as DMSO and sulfolane; alcohols such as methanol, ethanol, ethylene glycol, isopropanol and t-butanol; or a mixture thereof are set forth.

Reaction 2 is usually performed within a solvent. The limits to the reaction temperature are usually from −20 to 200° C., and the limits to the reaction time are usually from a moment to 72 hours. For the amount of the agents used in the reaction, based on 1 mole of α-dihalo compound utilized in reaction 1, a rate of 1 mole is the theoretical amount of compound [A1], but may be optionally altered to correspond to the condition of the reaction. Furthermore, the salt of compound [A1] (for example, hydrochloric acid salts or sulfuric acid salts) may utilized to correspond with the condition of the reaction.

As the solvent, aliphatic hydrocarbons such as hexane, heptane, ligroin, cyclohexane and petroleum ether; aromatic hydrocarbons such as benzene, toluene and xylene; halogenated hydrocarbons such as chloroform, carbon tetrachloride, dichloromethane, dichloroethane, chlorobenzene and dichlorobenzene; ethers such as diethyl ether, diisopropyl ether, dioxane, THF and ethylene glycol dimethyl ether; esters such as ethyl formate, ethyl acetate, butyl acetate and diethyl carbonate; nitro compounds such as nitromethane and nitrobenzene; nitriles such as acetonitrile and isobutylonitrile; acid amides such as formamide, DMF and acetamide; tertiary amines such as pyridine, triethylamine, diisopropylethylamine, N,N-dimethylaniline, N,N-diethylaniline and N-methylmorpholine; sulfur compounds such as DMSO and sulfolane; fatty acids such as formic acid, acetic acid and propionic acid; alcohols such as methanol, ethanol, ethylene glycol, isopropanol and t-butanol; water; or a mixture thereof are set forth.

After the completion of the reaction, the reaction mixture may be filtered to collect the precipitated crystals or may be subjected to the ordinary post-treatment such as extraction with an organic solvent and concentration, and if necessary, may be further purified by the procedure such as chromatography and recrystallization. Thus objective material can be isolated.

2) A method to produce compound [A3] from compound [A2]

Compound [A3] may be produced by reacting compound [A2] with the phosphorane compound having the formula $$Ar_3P=C(R^{100})COOR^{30}$$

wherein, $R^{100}$, $R^{30}$ and Ar have the same definition as mentioned above.

The said reaction is usually performed within a solvent. The limits to the reaction temperature are usually from −20 to 150° C., preferably from 0 to 100° C., and the limits to the reaction time are usually from a moment to 72 hours. For the amounts of the agents used in the reaction, based on 1 mole of compound [A2], a rate of 1 mole is the theoretical amount of phosphorane, but may be optionally altered to correspond to the condition of the reaction.

As the solvents that may be utilized, aliphatic hydrocarbons such as hexane, heptane, ligroin, cyclohexane and petroleum ether; aromatic hydrocarbons such as benzene, toluene and xylene; ethers such as diethyl ether, diisopropyl ether, dioxane, THF and ethylene glycol dimethyl ether; nitro compounds such as nitromethane and nitrobenzene; acid amides such as formamide, DMF and acetamide; tertiary amines such as pyridine, triethylamine, diisopropylethylamine, N,N-dimethylaniline, N,N- diethylaniline and N-methylmorpholine; sulfur compounds such as DMSO and sulfolane; alcohols such as methanol, ethanol, ethylene glycol, isopropanol and t-butanol; water; or a mixture thereof are set forth.

After the completion of the reaction, the reaction mixture may be subjected to distillation to remove the reaction solvent and then the residue may be subjected to chromatography, or the reaction mixture may be subjected to the ordinary post-treatment such as extraction with an organic solvent and concentration. If necessary, further purification such as chromatography and recrystallization may be conducted. Thus the objective material can be isolated.

3) A method to produce compound [A4] from compound [A3]

Compound [A4] may be produced by performing a intramolecular cyclization reaction with compound [A3] in the presence of an acid. The said reaction is usually performed within a solvent. The limits to the reaction temperature are usually from 0 to 200° C., preferably from 50 to 150° C., and the limits to the reaction time are usually from a moment to 72 hours.

As the acid, inorganic acids such as hydrochloric acid and sulfuric acid, or organic acids such as trifluoroacetic acid and p-toluenesulfonic acid may be set forth. The amount of the acid used in the reaction is ratio of a catalytic amount to an excess amount based on 1 mole of compound [A3].

As the solvent, aliphatic hydrocarbons such as hexane, heptane, ligroin, cyclohexane and petroleum ether; aromatic hydrocarbons such as benzene, toluene and xylene; halogenated hydrocarbons such as chloroform, carbon tetrachloride, dichloromethane, dichloroethane, chlorobenzene and dichlorobenzene; ethers such as diethyl ether, diisopropyl ether, dioxane, THF and ethyleneglycol dimethyl ether; ketones such as acetone, methylethyl ketone, methylisobutyl ketone, isophorone and cyclohexanone; nitro compounds such as nitromethane and nitrobenzene; sulfur compounds such as DMSO and sulfolane; fatty acids such as formic acid, acetic acid and propionic acid; alcohols such as methanol, ethanol, ethylene glycol, isopropanol and t-butanol; water, or a mixture of thereof may be set forth.

After the completion of the reaction, the reaction mixture may be filtered to collect the precipitated crystals or may be subjected to the ordinary post-treatment such as extraction with an organic solvent and concentration, and if necessary, may be further purified by the procedure such as chromatography and recrystallization. Thus objective material can be isolated.

(production method 5)
A production method according to the following scheme.

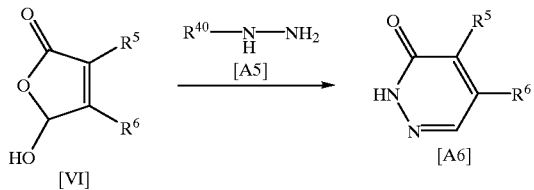

wherein, $R^5$ and $R^6$ have the same definition as mentioned above, and $R^{40}$ represents hydrogen, carbamoyl, formyl or $C_1$–$C_6$ alkylcarbonyl such as acetyl and propionyl.

Compound [A6] may be produced by reacting compound [VI] with compound [A5].

The reaction is usually performed within a solvent. The limits to the reaction temperature are usually from 0 to 120° C., and the limits to the reaction time are usually from a moment to 72 hours. For the amounts of the agents used in the reaction, based on 1 mole compound [VI], a rate of 1 mole is the theoretical amount of compound [A5], but may be optionally altered to correspond to the condition of the reaction.

As the solvent, organic acids such as acetic acid and propionic acid may be set forth.

After the completion of the reaction, the reaction mixture may be poured into water to correct the precipitated crystals or may be subjected to the ordinary post-treatment such as extraction with an organic solvent and concentration. If necessary, further purification procedure such as chromatography and recrystallization may be conducted. Thus the objective material may be isolated.

The benzyl derivative of Chemical Formula 6 may be a product from the market, for example; public knowledge from U.S. Pat. No. 5,683,966, the specification of international patent publication WO 95/04461, international patent publication WO 97/35845, and international patent publication WO 95/47607; may be produced by corresponding to the methods disclosed in thereof; or produced by corresponding to the method disclosed in Jikken Kagaku Kouza (Maruzen Company Ltd.) 4th edition, volume 19, pages 364 to 482.

Compound [V] may be product from the market, or it may be produced from a compound which is produced by corresponding to the method disclosed in Synthetic Organic Chemistry (John Wiley & Sons, Inc.) 5th edition, page 560.

Moreover, compound [I] may be a product from the market, or it may be produced by corresponding to the method disclosed in Jikken Kagaku Kouza (Maruzen Company Ltd.) $4^{th}$ edition, volume 20, pages 338 to 342 for example, or by corresponding to the following method of production method 6.

(production method 6)
A production method that complies to the following scheme given in Chemical Formula 9:
[Chemical Formula 9]

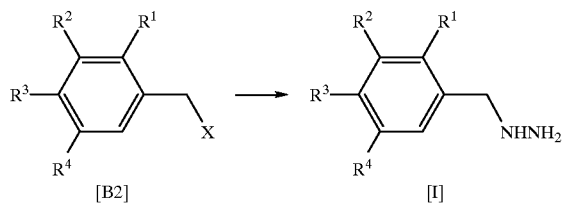

wherein, $R^1$, $R^2$, $R^{3,}$ $R^4$ and X have the same definition as mentioned above.

Compound [I] may be produced by reacting compound [B2] and $NH_2NH_2$ within a solvent and in the presence of a base. The $NH_2NH_2$ utilized in the said reaction may also be reacted as a hydrochloric acid salt, sulfuric acid salt, or a hydrate amount of $NH_2NH_2$: based on 1 mole of compound [B2], a rate from 1 to 10 moles base: sodium hydroxide, potassium carbonate amount of base: based on 1 mole of compound [B2], a rate from 1 to 10 moles
solvent: ethanol, etc.
temperature: –20 to 100° C.
time: a moment to 24 hours After the completion of the reaction, the reaction mixture may be subjected to distillation to remove the reaction solvent and then the residue may be subjected to chromatography or the reaction mixture may be poured into water and then the ordinary post-treatment such as extraction with an organic solvent and concentration may be performed. If necessary, the further purification procedure such as chromatography and recrystallization may be subjected. Thus the objective material can be isolated.

The present invention compounds possess herbicidal activity and in addition, some of them show excellent selectivity between crops and weeds. The present invention compounds possess excellent herbicidal activity against the following variation of weeds that cause problems in foliar or soil treatment on upland fields.

Polygonaceous weeds:
wild buckwheat (*Polygonum convolvulus*), pale smartweed (*Polygonum lapathifolium*), pennsylvania smartweed (*Polygonum pensylvanicum*), ladysthumb (*Polygonum persicaria*), curly dock (*Rumex crispus*), broadleaf dock (*Rumex obtusifolius*), Japanese knotweed (*Polygonum cuspidatum*)

Portulacaceous weeds:
common purslane (*Portulaca oleracea*)

Caryophyllaceous weeds:
common chickweed (*Stellaria media*)

Chenopodiaceous weeds:
common lambsquarters (*Chenopodium album*), kochia (*Kochia scoparia*)

Amaranthaceous weeds:
redroot pigweed (*Amaranthus retroflexus*), smooth pigweed (*Amaranthus hybridus*)

Cruciferous (brassicaceous) weeds:
wild radish (*Raphanus raphanistrum*), wild mustard (*Sinapis arvensis*), shepherdpurse (*Capsella bursa-pastoris*)

Leguminous (fabaceous) weeds:
hemp sesbania (*Sesbania exaltata*), sicklepod (*Cassia obtusifolia*), Florida beggarweed (*Desmodium tortuosum*), white clover (*Trifolium repens*)

Malvaceous weeds:
velvetleaf (*Abutilon theophrasti*), prickly sida (*Sida spinosa*)

Violaceous weeds:
field pansy (*Viola arvensis*), wild pansy (*Viola tricolor*)

Rubiaceous weeds:
catchweed bedstraw (cleavers) (*Galium aparine*)

Convolvulaceous weeds:
ivyleaf morningglory (*Ipomoea hederacea*), tall morningglory (*Ipomoea purpurea*), entireleaf morningglory (*Ipomoea hederacea* var. *integriuscula*), pitted morningglory (*Ipomoea lacunosa*), field bindweed (*Convolvulus arvensis*)

Labiate weeds:
red deadnettle (*Lamium purpureum*), henbit (*Lamium amplexicaule*)

Solanaceous weeds:
jimsonweed (*Datura stramonium*), black nightshade (*Solanum nigrum*)

Scrophulariaceous weeds:
birdseye speedwell (*Veronica persica*), ivyleaf speedwell (*Veronica hederaefolia*)

Composite weeds:
common cocklebur (*Xanthium pensylvanicum*), common sunflower (*Helianthus annuus*), scentless chamomile (*Matricaria perforata* or *inodora*), corn marigold (*Chrysanthemum segetum*), pineappleweed (*Matricaria matricarioides*), common ragweed (*Ambrosia artemisiifolia*), giant ragweed (*Ambrosia trifida*), horseweed (*Erigeron canadensis*), Japanese mugwort (*Artemisia princeps*), tall goldenrod (*Solidago altissima*)

Boraginaceous weeds:
forget-me-not (*Myosotis arvensis*)

Asclepiadaceous weeds:
common milkweed (*Asclepias syriaca*)

Euphorbiaceous weeds:
sun spurge (*Euphorbia helioscopia*), spotted spurge (*Euphorbia maculata*)

Graminaceous weeds:
barnyardgrass (*Echinochloa crus-galli*), green foxtail (*Setaria viridis*), giant foxtail (*Setaria faberi*), large crabgrass (*Digitaria sanguinalis*), goosegrass (*Eleusine indica*), annual bluegrass (*Poa annua*), blackgrass (*Alopecurus myosuroides*), wild oats (*Avena fatua*), johnsongrass (*Sorghum halepense*), quackgrass (*Agropyron repens*), downy brome (*Bromus tectorum*), bermudagrass (*Cynodon dactylon*), fall panicum (*Panicum dichotomiflorum*), Texas panicum (*Panicum texanum*), shattercane (*Sorghum vulgare*)

Commelinaceous weeds:
common dayflower (*Commelina communis*)

Equisetaceous weeds:
field horsetail (*Equisetum arvense*)

Cyperaceous weeds:
rice flatsedge (*Cyperus iria*), purple nutsedge (*Cyperus rotundus*), yellow nutsedge (*Cyperus esculentus*)

Furthermore, some of the present invention compounds exhibit no significant phytotoxicity on the main crops such as corn (*Zea mays*), wheat (*Triticum aestivum*), barley (*Hordeum vulgare*), rice (*Oryza sativa*), sorghum (*Sorghum bicolor*), soybean (*Glycine max*), cotton (Gossypium spp.), sugar beet (*Beta vulgaris*), peanut (*Arachis hypogaea*), sunflower (*Helianthus annuus*), and canola (*Brassica napus*); horticultural crops such as flowers and ornamental plants; and vegetables. Various weeds that may cause some trouble in the no-tillage cultivation of soybean (*Glycine max*), corn (*Zea mays*), wheat (*Triticum aestivum*), or the like may be efficaciously controlled by the present invention compounds. Furthermore, some of the present invention compounds exhibit no significant phytotoxicity on the crops.

The present invention compounds also have herbicidal activity against various weeds which may cause some trouble in the flooding treatment on paddy fields, such as the listed below.

Graminaceous weeds:
barnyardgrass (*Echinochloa oryzicola*)

Scrophulariaceous weeds:
common falsepimpernel (*Lindernia procumbens*)

Lythraceous weeds:
Indian toothcup (*Rotala indica*), red stem (*Ammannia multiflora*)

Elatinaceous weeds:
waterwort (*Elatine triandra*)

Cyperaceous weeds:
smallflower umbrella sedge (*Cyperus difformis*), hardstem bulrush (*Scirpus juncoides*), needle spikerush (*Eleocharis acicularis*), water nutgrass (*Cyperus serotinus*), water chestnut (*Eleocharis kuroguwai*)

Pontederiaceous weeds:
monochoria (*Monochoria vaginalis*)

Alismataceous weeds:
arrowhead (*Sagittaria pygmaea*), arrowhead (*Sagittaria trifolia*), waterplantain (*Alisma canaliculatum*)

Potamogetonaceous weeds:
roundleaf pondweed (*Potamogeton distinctus*)

Umbelliferous weeds:
watercelery sp. (*Oenanthe javanica*)

Furthermore, some of the present invention compounds exhibit no significant phytotoxicity on transplanted paddy rice.

The present invention compounds can also control a wide variety of weeds which grow or will grow in the orchards, grasslands, lawns, forests, waterways, canals, or other uncultivated lands. In addition, the present invention compounds also have herbicidal activity against various aquatic weeds, such as water hyacinth (Eichhornia crassipes), which grow or will grow by waterways or canals.

The present invention compounds have substantially the same characteristics as those of the herbicidal compounds disclosed in the specification of international patent publication WO 95/34659. In the case of cultivating crops wherein tolerance is bestowed to the said crops by introducing a herbicide tolerance gene described in said specification, the present invention compounds can be used at larger amounts than those used when ordinary crops without tolerance are cultivated, thus making it possible to control other unfavorable weeds more effectively.

When one of the present invention compounds is used as the active ingredient of a herbicide, the present invention compound is usually mixed with solid or liquid carriers or diluents, surfactants, and other auxiliary agents to formulate emulsifiable concentrates, wettable powders, flowables, granules, concentrated emulsions, water-dispersible granules, or other formulations.

These formulations may comprise a compound of present invention as an active ingredient at an amount from 0.001% to 80% by weight, preferably from 0.005% to 70% by weight.

The solid carrier or diluent may include, for example, mineral fine powders such as kaolin clay, attapulgite clay, bentonite, acid clay, pyrophyllite, talc, diatomaceous earth, and calcite; organic fine powders such as walnut shell powder; water-soluble organic fine powders such as urea; fine powders of inorganic salts such as ammonium sulfate; and fine powders of synthetic hydrated silicon oxide.

The liquid carrier or diluent may include, for example, aromatic hydrocarbons such as methylnaphthalene, phenylxylylethane and alkylbenzene (e.g., xylene); alcohols such as isopropanol, ethylene glycol and 2-ethoxyethanol; esters such as dialkyl ester phthalate; ketones such as acetone, cyclohexanone and isophorone; mineral oils such as machine oil; vegetable oils such as soybean oil and cottonseed oil; dimethylsulfoxide, N,N-dimethylformamide, acetonitrile, N-methylpyrrolidone and water.

As the surfactant used for emulsion, dispersing or spreading; anionic surfactants such as alkylsulfate salts, alkylsulfonate salts, alkylarylsulfonate salts, dialkylsulfosuccinate salts and polyoxyethylene alkylarylether phosphate salts and nonionic surfactants such as polyoxyethylene alkylether, polyoxyethylene alkylarylether, polyoxyethylene polyoxypropylene block copolymers, sorbitan fatty acid esters and polyoxyethylene sorbitan fatty acid ester are set forth.

Lignin sulfonates, alginates, polyvinyl alcohol, gum arabic, CMC (carboxymethylcellulose), and PAP (isopropyl acid phosphate) and the like are set forth as the other possible auxiliary agents for formulation.

The present invention compounds are usually formulated and then used for soil treatment before or after the weed has emerged from the soil, for foliar treatment or for flooding treatment. The soil treatment may include a soil surface treatment and a soil incorporation. The foliar treatment may include application over the plants and directed application in which it is applied only to weeds, so as to keep the same off the crop plants.

Furthermore, by intermixing with other herbicides, there are situations wherein an enhanced herbicidal efficacy is confirmed. Furthermore, the present invention compounds may be used in a mixture or in combination with insecticides, acaricides, nematocides, fungicides, bactericides, plant growth regulators, fertilizers, and soil improvements.

Examples of the herbicides include atrazine, cyanazine, dimethametryn, metribuzin, prometryn, simazine, simetryn, chlorotoluron, diuron, daimuron, fluometuron, isoproturon, linuron, methabenzthiazuron, bromoxynil, ioxynil, ethalfluralin, pendimethalin, trifluralin, acifluorfen, acifluorfen-sodium, bifenox, chlomethoxynil, fomesafen, lactofen, oxadiazon, oxadiargyl, oxyfluorfen, carfentrazone-ethyl, flumiclorac-pentyl, flumioxazine, fluthiacet-methyl, sulfentrazone, thidiazimin, azafenidin, pyraflufen-ethyl, cinidon-ethyl, difenzoquat, diquat, paraquat, 2,4-D, 2,4-DB, DCPA, MCPA, MCPB, clomeprop, clopyralid, dicamba, dithiopyr, fluroxypyr, mecoprop, naploanilide, phenothiol, quinclorac, triclopyr, thiazopyr, acetochlor, alachlor, butachlor, diethatyl-ethyl, metolachlor, pretilachlor, propachlor, bensulfuron-methyl, chlorsulfuron, chlorimuron-ethyl, halosulfuron-methyl, metsulfuron-methyl, nicosulfuron, primisulfuron-methyl, pyrazosulfuron-ethyl, sulfometuron-ethyl, thifensulfuron-methyl, triasulfuron, tribenuron-methyl, oxasulfuron, iodosulfuron, azimsulfuron, cloransulam-methyl, cyclosulfamuron, flumetsulam, flupyrsulfuron, flazasulfuron, imazosulfuron, metosulam, diclosulam, prosulfuron, rimsulfuron, triflusulfuron-methyl, ethoxysulfuron, sulfosulfuron, imazamethabenz-methyl, imazapyr, imazaquin, imazethapyr, imazameth, imazamox, flucarbazone, pyribenzoxim, bispyribac-sodium, pyriminobac-methyl, pyrithiobac-sodium, alloxydim-sodium, clethodim, sethoxydim, tralkoxydim, tepraloxydim, dichlofop-methyl, fenoxaprop-ethyl, fenoxaprop-p-ethyl, fluazifop-butyl, fluazifop-p-butyl, haloxyfop-methyl, quizalofop-p-ethyl, cyhalofop-butyl, clodinafop-propargyl, benzofenap, clomazone, diflufenican, norflurazon, pyrazolate, pyrazoxyfen, flurtamone, isoxaflutole, sulcotrione, mesotrione, isoxachlortole, glufosinate-ammonium, glyphosate, bentazone, benthiocarb, bromobutide, butamifos, butylate, dimepiperate, dimethenamid, fentrazamide, DSMA, EPTC, esprocarb, isoxaben, mefenacet, molinate, MSMA, piperophos, pyributicarb, propanil, pyridate, triallate, cafenstrol, flupoxam, fluthiamide, diflufenzopyr, triaziflam, pentoxazone, epoprodan, metobenzuron, oxaziclomefone, isopropazol, and indanofan.

The above compounds are disclosed in the catalog of Farm Chemicals Handbook, 1995 (published by Meister Publishing Company); AG CHEM NEW COMPOUND REVIEW, VOL. 13, 1995, VOL. 15, 1997 and VOL. 16, 1998 (published by AG CHEM INFORMATION SERVICES); and "Josouzai Kenkyu Souran" (published by Hakuyu-sha).

In the case when the present invention compound is utilized as an active ingredient of an herbicide, the application amount may vary with the weather conditions, formulation types, application timing, application method, soil conditions, objective crop or crops, objective weed or weeds, and so on, but is usually applied at 0.0 g to 20,000 g per hectare, preferably 1 g to 2,000 g per hectare. When the present invention compound is formulated into emulsifiable concentrates, wettable powders, flowables, concentrated emulsions, water-dispersible granules, or the like, the said formulations are applied by diluting the present compound invention usually in 10L to 1,000L (if necessary, the water may include adjuvant such as a spreading agent) so the prescribed amount of the active ingredient can be applied to each hectare. Granule formulations and some types of flowables are usually applied without diluting.

The adjuvant which can be used herein, if necessary, may include, in addition to the surfactants as described above, polyoxyethylene resin acids (esters), lignin sulfonates, abietates, dinaphthylmethanedisulfonates, crop oil concentrates, and vegetable oils such as soybean oil, corn oil, cottonseed oil, and sunflower oil. The present invention compounds can also be used as the active ingredients of harvesting aids such as defoliants and desiccants for cotton (Gossipyum spp.), and desiccants for potato (*Solanum tuberosum*). In these cases, the present invention compounds are usually formulated in the same manner as the case where they are used as the active ingredients of herbicides, and may be used alone or in admixture with other harvesting aids for foliar treatment before harvesting the crops.

Hereinafter, the present invention is explained more specifically by means of the production examples, formulation examples and test examples, but the said examples do not limit the present invention in any way.

Production Example 1 (the production of the present invention compound 1–1)

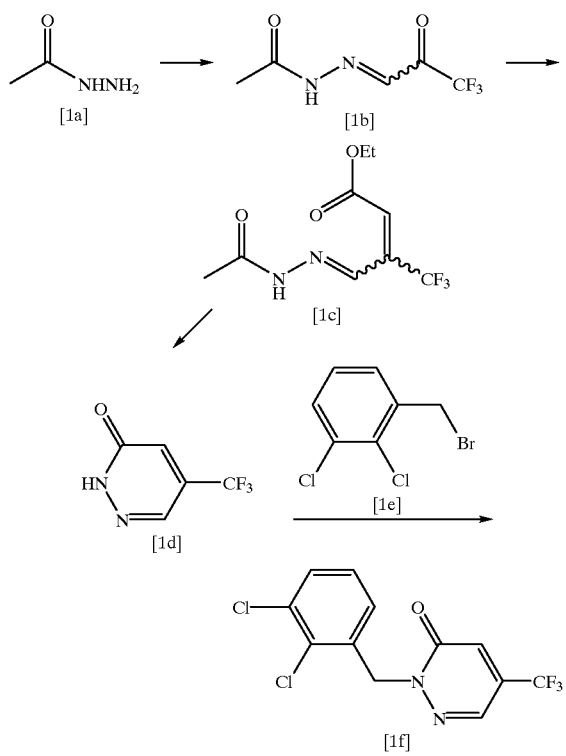

1) Method to produce compound [1b] from compound [1a]

In a solution of 2.2 g of 1,1-dibromo-3,3,3-trifluoroacetone and 25 mL of water, 4.9 g of sodium acetate trihydrate was incorporated, and was heated for 1.5 hours at 10 80° C. After cooling the reaction mixture to room temperature, 0.40 g of compound [1a] was incorporated. After stirring the mixture at room temperature for 1 hour, water was added, then extracted with diethyl ether. After drying the obtained organic layer with magnesium sulfate anhydride, the said organic layer was concentrated under reduced pressure to give 0.65 g of compound [1b].

[$^1$H-NMR(300 MHz, CDCl$_3$, TMS δ (ppm)); 2.38 (3H, s), 7.41 (1H, br), 10.30 (1H, br)]

2) Method to produce compound [1c] from compound [1b]

In a solution of 0.64 g of compound [1b] and 10 mL of tetrahydrofuran, 1.4 g of Ph$_3$P=CHCO$_2$C$_2$H$_5$ wherein Ph represents phenyl was added under ice cooling, and then stirred at room temperature for 2 hours. After the completion of the reaction, the obtained mixture had water added and was extracted with diethylether. After drying the organic layer by utilizing magnesium sulfate anhydride, the said organic layer was concentrated under reduced pressure and had the residue subjected to silica gel chromatography to give 0.75 g of compound [1c]. m.p. 76.5° C.

3) Method to produce compound [1d] from compound [1c]

Ten millimeters (10 mL) of concentrated hydrochloric acid was added to 0.75 g of compound [1c]. The mixture was stirred for 30 minutes at room temperature, and was subsequently stirred for 2 hours while heating under reflux. After then, water was added into the reaction mixture and the mixture obtained was extracted with diethylether. After drying the organic layer by utilizing magnesium sulfate anhydride, the said organic layer was concentrated under reduced pressure to give 0.31 g of compound [1d]. m.p. 98.2° C.

4) Method to produce compound [1f] from compound [1d]

In a solution of 0.30 g of compound [1d], 5 mL of N,N-dimethylformamide and 0.28 g of potassium carbonate, 0.50 g of compound [1e] was dropped and was stirred for 30 minutes at room temperature. After then, diluted hydrochloric acid was poured into the reaction mixture and the obtained mixture was extracted with ethyl acetate. The organic layer was washed by utilizing an aqueous solution saturated with sodium chloride, dried by utilizing magnesium sulfate anhydride, and concentrated under reduced pressure. The resulting residue was subjected to column chromatography to give 0.45 g of compound [1f] (the present invention compound 1–1). m.p. 93.5° C. compound [1e] was produced by the following production method To a solution of 5 mL of 2,3-dichlorotoluene and 50 mL of chloroform, 7.13 g of N-bromosuccinimide and a catalytic amount of 2,2'-azobisisobutylonitrile were added, then the obtained mixture was stirred for 1 hour at room temperature, and heated under reflux for 1.5 hours. Afterwards, an aqueous solution of sodium sulfite was added to the reaction mixture, and the obtained mixture was extracted with chloroform. The organic layer was dried by utilizing magnesium sulfate anhydride, then concentrated under reduced pressure, and the resulting residue was subjected to column chromatography to give 2.52 g of compound [1e].

[$^1$H-NMR(300MHz, CDCl$_3$, TMS δ (ppm)); 4.60 (2H, s), 7.19 (1H, t, J=7.8 Hz), 7.36 (1H, dd, J=7.8 Hz, 1,4 Hz), 7.43 (1H, dd, J=7.8 Hz, 1.4 Hz)]

Production Example 2 (production of the present invention compound 2-1)

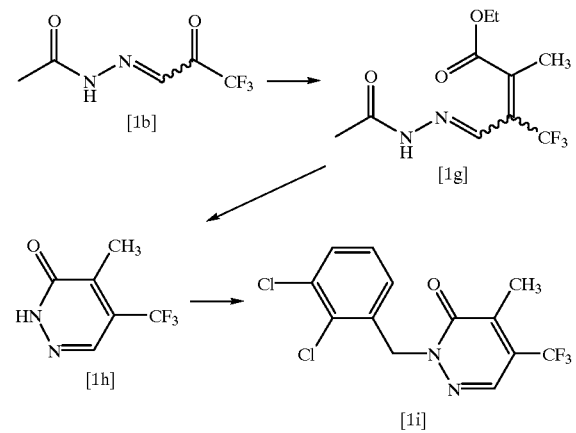

1) Method to produce compound [1 g] from compound [1b]

To a solution of 13 g of compound [1b] and 130 mL of tetrahydrofuran, 39 g of Ph$_3$P=C(CH$_3$)CO$_2$C$_2$H$_5$ wherein Ph represents phenyl was added, and the obtained mixture was then left overnight. After stirring at 40° C. for 3 hours, the mixture had water added and was then extracted with ethyl acetate. Afterwards, the organic layer was washed by utilizing an aqueous solution saturated with sodium chloride, dried by utilizing magnesium sulfate anhydride, and then concentrated under reduced pressure. The resulting residue was subjected to silica gel column chromatography to give 6.0 g of compound [1g]. m.p. 94.5° C.

2) Method to produce compound [1h] from compound [1 g]

Eighty milliliters (80 mL) of concentrated hydrochloric acid was added to 5.5 g of compound [1g], then the obtained mixture was stirred for 3 hour while being heated under reflux. Afterwards, water was added to the reaction mixture and the resultant was extracted with ethyl acetate. The organic layer was washed by utilizing an aqueous solution saturated with sodium chloride, dried by utilizing magnesium sulfate anhydride, and then concentrated under reduced pressure. The resulting residue was subjected to silica gel column chromatography to give 0.9 g of compound [1h].

[$^1$H-NMR(300 MHz, CDCl$_3$, TMS δ (ppm)); 2.39 (3H, q, J=1.8 Hz), 7.96 (1H, s), 12.35 (1H, br)]

3) Method to produce compound [1i] from compound [1h]

To a solution of 0.40 g of compound [1h], 10 mL of N,N-dimethylformamide and 0.65 g of 2,3-dichlorobenzyl bromide, 0.38 g of potassium carbonate was added under ice cooling, and the obtained mixture was then left overnight at a room temperature. The reaction mixture then had diluted hydrochloric acid added and was then extracted with ethyl acetate. The organic layer was washed by utilizing an aqueous solution saturated with sodium chloride, dried by utilizing magnesium sulfate anhydride, and then concentrated under reduced pressure. The resulting residue was washed by utilizing 2-propanol to give 0.42 g of compound [1i] (the present invention compound 2-1).
m.p. 105.8° C.

Production Example 3 (the production of intermediate compound [1d])

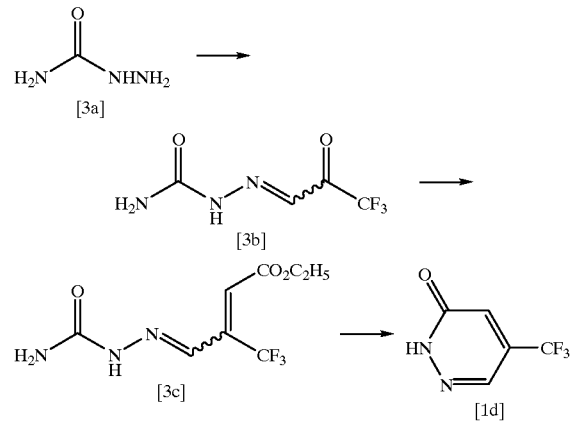

1) Method to produce compound [3b] from compound [3a]

To the solution of 158 g of 1,1-dibromo-3,3,3-trifluoroacetone and 1.5L of water, 318 g of sodium acetate trihydrate was incorporated, and the obtained mixture was stirred while heating at 80° C. for 1.5 hours. After cooling the mixture to the room temperature, 50 g of compound [3a] was added, and then the obtained mixture was stirred at room temperature for 5.5 hours. The precipitated crystals were collected by filtration and dried under reduced pressure to give 74 g of the crude compound [3b].

2) Method to produce compound [3c] from compound [3b]

To the solution of 7.0 g of compound [3b] and 50 ml of tetrahydrofuran, 13.3 g of Ph$_3$P=CHCO$_2$C$_2$H$_5$ [wherein Ph represents phenyl.] was added, and the obtained mixture was stirred at room temperature for 3 hours and left overnight. After the completion of the reaction, the reaction mixture was concentrated. The obtained residue was dissolved in t-butyl methyl ether to remove insoluble matters and the obtained organic layer was dried with magnesium sulfate and then concentrated to give 5.7 g of the compound [3c].

[$^1$H-NMR(250 MHz,CDCl$_3$, TMS δ (ppm)); 1.33(3H,t,J=7.1 Hz),4.27(2H,q,J=7.1 Hz),6.51(1H,s),8.67(1H,s),9.93 (1H,br)]

3) Method to compound [1d] from compound [3c]

To 57 g of compound [3c], 200ml of concentrated hydrochloric acid was added, and the obtained mixture was stirred while heating under reflux for 4.5 hours. The reaction mixture was cooled to room temperature and the precipitated crystals were collected by filtration to give 21.5 g of compound [1d].

Hereinafter, the present invention compounds are set forth in tables 1 through 5 with assigned compound numbers, but the present invention compounds are not limited to the following.

The compound represented by the following formula:

Chemical Formula 10

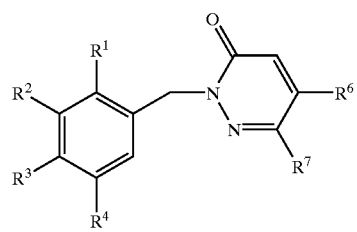

TABLE 1

| Compound No | R$^1$ | R$^2$ | R$^3$ | R$^4$ | R$^6$ | R$^7$ |
|---|---|---|---|---|---|---|
| 1-1 | Cl | Cl | H | H | CF$_3$ | H |
| 1-2 | H | Cl | H | Cl | CF$_3$ | H |
| 1-3 | Cl | Cl | Cl | H | CF$_3$ | H |
| 1-4 | H | H | NO$_2$ | OCH$_2$CO$_2$Et | CF$_3$ | H |
| 1-5 | Cl | Cl | H | OCH$_3$ | CF$_3$ | H |
| 1-6 | Cl | Cl | H | CH$_3$ | CF$_3$ | H |
| 1-7 | Cl | Cl | CF$_3$ | H | CF$_3$ | H |
| 1-8 | H | H | Cl | OCH$_2$CO$_2$Et | CF$_3$ | H |
| 1-9 | Cl | Cl | H | OCH(CH$_3$)$_2$ | CF$_3$ | H |
| 1-10 | Cl | CN | NO$_2$ | H | CF$_3$ | H |
| 1-11 | Cl | Cl | H | H | CF$_2$Cl | H |
| 1-12 | Cl | Cl | H | Cl | CF$_2$CF$_3$ | H |
| 1-13 | Cl | Cl | OCH(CH$_3$) | H | CF$_3$ | H |
| 1-14 | H | H | NO$_2$ | OEt | CF$_3$ | H |
| 1-15 | Cl | Cl | NH$_2$ | H | CF$_3$ | H |
| 1-16 | Cl | Cl | H | Cl | CF$_3$ | H |
| 1-17 | H | H | NO$_2$ | OMe | CF$_3$ | H |
| 1-18 | Cl | Cl | H | NH$_2$ | CF$_3$ | H |
| 1-19 | Cl | Cl | H | H | CF$_3$ | CH$_3$ |
| 1-20 | Cl | Cl | CH$_2$OCH$_3$ | H | CF$_3$ | H |
| 1-21 | H | H | NO$_2$ | CO$_2$Me | CF$_3$ | H |
| 1-22 | H | H | Cl | CO$_2$Et | CF$_3$ | H |
| 1-23 | H | H | Cl | OCH(Me)CO$_2$Et | CF$_3$ | H |
| 1-24 | Cl | Cl | H | Cl | CF$_2$Cl | H |
| 1-25 | H | H | Cl | OEt | CF$_3$ | H |

TABLE 2

| Compound No | R¹ | R² | R³ | R⁴ | R⁶ | R⁷ |
|---|---|---|---|---|---|---|
| 1-26 | H | H | H | OCH$_2$CO$_2$Et | CF$_3$ | H |
| 1-27 | H | H | NO$_2$ | OCH(Me)CO$_2$Et | CF$_3$ | H |
| 1-28 | Cl | Cl | OCH$_3$ | H | CF$_3$ | H |
| 1-29 | H | H | Cl | OMe | CF$_3$ | H |
| 1-30 | Cl | OMe | NO$_2$ | H | CF$_3$ | H |
| 1-31 | H | H | H | OCH(Me)CO$_2$Et | CF$_3$ | H |
| 1-32 | Cl | Cl | H | Cl | CF$_2$CH$_3$ | H |
| 1-33 | Cl | Cl | H | CF$_3$ | CF$_3$ | H |
| 1-34 | Cl | Cl | H | CH$_2$OCH$_3$ | CF$_3$ | H |
| 1-35 | Cl | Cl | CH$_3$ | H | CF$_3$ | H |
| 1-36 | Cl | Cl | H | H | CF$_2$Cl | CH$_3$ |

The compound represented by the following formula:

Chemical Formula 11

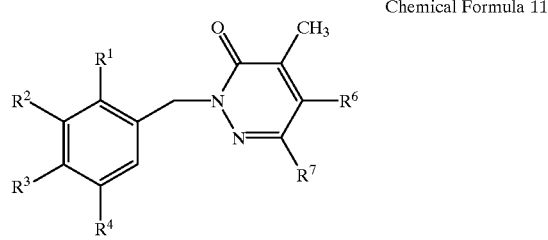

TABLE 3

| Compound No | R¹ | R² | R³ | R⁴ | R⁶ | R⁷ |
|---|---|---|---|---|---|---|
| 2-1 | Cl | Cl | H | H | CF$_3$ | H |
| 2-2 | H | Cl | H | Cl | CF$_3$ | H |
| 2-3 | Cl | Cl | Cl | H | CF$_3$ | H |
| 2-4 | H | H | NO$_2$ | OCH$_2$CO$_2$Et | CF$_3$ | H |
| 2-5 | Cl | Cl | H | OCH$_3$ | CF$_3$ | H |
| 2-6 | Cl | Cl | H | CH$_3$ | CF$_3$ | H |
| 2-7 | Cl | Cl | CF$_3$ | H | CF$_3$ | H |
| 2-8 | H | H | Cl | OCH$_2$CO$_2$Et | CF$_3$ | H |
| 2-9 | Cl | Cl | H | OCH(CH$_3$)$_2$ | CF$_3$ | H |
| 2-10 | Cl | CN | NO$_2$ | H | CF$_3$ | H |
| 2-11 | Cl | Cl | H | H | CF$_2$Cl | H |
| 2-12 | Cl | Cl | H | Cl | CF$_2$CF$_3$ | H |
| 2-13 | Cl | Cl | OCH(CH$_3$) | H | CF$_3$ | H |
| 2-14 | H | H | NO$_2$ | OEt | CF$_3$ | H |
| 2-15 | Cl | Cl | NH$_2$ | H | CF$_3$ | H |
| 2-16 | Cl | Cl | H | Cl | CF$_3$ | H |
| 2-17 | H | H | NO$_2$ | OMe | CF$_3$ | H |
| 2-18 | Cl | Cl | H | NH$_2$ | CF$_3$ | H |
| 2-19 | Cl | Cl | H | H | CF$_3$ | CH$_3$ |
| 2-20 | Cl | Cl | CH$_2$OCH$_3$ | H | CF$_3$ | H |
| 2-21 | H | H | NO$_2$ | CO$_2$Me | CF$_3$ | H |
| 2-22 | H | H | Cl | CO$_2$Et | CF$_3$ | H |
| 2-23 | H | H | Cl | OCH(Me)CO$_2$Et | CF$_3$ | H |
| 2-24 | Cl | Cl | H | Cl | CF$_2$Cl | H |
| 2-25 | H | H | Cl | OEt | CF$_3$ | H |

TABLE 4

| Compound No | R¹ | R² | R³ | R⁴ | R⁶ | R⁷ |
|---|---|---|---|---|---|---|
| 2-26 | H | H | H | OCH$_2$CO$_2$Et | CF$_3$ | H |
| 2-27 | H | H | NO$_2$ | OCH(Me)CO$_2$Et | CF$_3$ | H |
| 2-28 | Cl | Cl | OCH$_3$ | H | CF$_3$ | H |
| 2-29 | H | H | Cl | OMe | CF$_3$ | H |
| 2-30 | Cl | OMe | NO$_2$ | H | CF$_3$ | H |
| 2-31 | H | H | H | OCH(Me)CO$_2$Et | CF$_3$ | H |
| 2-32 | Cl | Cl | H | Cl | CF$_2$CH$_3$ | H |
| 2-33 | Cl | Cl | H | CF$_3$ | CF$_3$ | H |

TABLE 4-continued

| Compound No | R¹ | R² | R³ | R⁴ | R⁶ | R⁷ |
|---|---|---|---|---|---|---|
| 2-34 | Cl | Cl | H | CH$_2$OCH$_3$ | CF$_3$ | H |
| 2-35 | Cl | Cl | CH$_3$ | H | CF$_3$ | H |
| 2-36 | Cl | Cl | H | H | CF$_2$Cl | CH$_3$ |

The compound represented by the following formula:

Chemical Formula 12

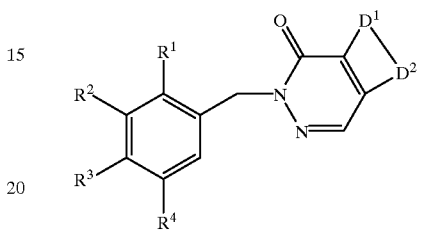

TABLE 5

| Compound No | R¹ | R² | R³ | R⁴ | D¹ | D² |
|---|---|---|---|---|---|---|
| 3-1 | Cl | Cl | H | H | CH$_2$CH$_2$CH$_2$ | CH$_2$ |
| 3-2 | H | Cl | H | Cl | CH$_2$CH$_2$CH$_2$ | CH$_2$ |
| 3-3 | Cl | Cl | Cl | H | CH$_2$CH$_2$CH$_2$ | CH$_2$ |
| 3-4 | Cl | Cl | H | Cl | CH$_2$CH$_2$CH$_2$ | CH$_2$ |
| 3-5 | Cl | Cl | H | H | CH$_2$CH$_2$ | CH$_2$ |
| 3-6 | H | Cl | H | Cl | CH$_2$CH$_2$ | CH$_2$ |
| 3-7 | Cl | Cl | H | H | CH$_2$CH$_2$CH$_2$ | CF$_2$ |
| 3-8 | H | Cl | H | Cl | CH$_2$CH$_2$CH$_2$ | CF$_2$ |
| 3-9 | Cl | Cl | Cl | H | CH$_2$CH$_2$CH$_2$ | CF$_2$ |
| 3-10 | Cl | Cl | H | Cl | CH$_2$CH$_2$CH$_2$ | CF$_2$ |

"Me" and "Et" in the above tables represent methyl and ethyl, respectively.

Physical data of some of the above-mentioned present invention compounds are as follows:

Compound 1-2: m.p. 115.5° C.
Compound 1-9: m.p. 99.1° C.
Compound 1-16: m.p. 111.3° C.
Compound 1-17: m.p. 110.5° C.
Compound 1-21: m.p. 92.8° C.
Compound 1-31:
  $^1$H-NMR (300 MHz, CDCl$_3$, TMS δ (ppm)) ; 1.25(3H,t, J=7.2 Hz), 1.58–1.62(3H,m), 4.21(2H,q,J=7.2 Hz), 4.73(1H,q,J=6.9 Hz), 5.29(2H,s), 6.80(1H,dd,J=2.2 Hz, 8.2 Hz), 6.95–6.97(1H,m), 7.03(1H,d,J=7.6 Hz), 7.15–7.17(1H,m), 7.20–7.24(1H,m), 7.90(1H,d,J=2.2 Hz)

Compound 3-4:
  $^1$H-NMR (300 MHz, CDCl$_3$, TMS δ (ppm)); 1.76–1.83 (4H,m), 2.55–2.60(4H,m), 5.40(2H,s), 6.93(1H,d,J=2.3 Hz), 7.39(1H,d,J=2.3 Hz), 7.55(1H,s)

Hereinafter, the formulation examples are given. The present invention compounds are now given with their assigned numbers from tables 1 through 5. Parts represents parts by weight.

Formulation Example 1

Fifty (50) parts each of the present invention compound 1-1, 1-2, 1-9, 1-16, 1-17, 1-21, 2-1 and 3-4,3 parts of calcium ligninsulfonate, 2 parts of sodium laurylsulfate and 45 parts of synthetic hydrated silicon oxide are pulverized and mixed to obtain wettable powders for each compound.

Formulation Example 2

Ten (10) parts each of the present invention compound 1-1, 1-2, 1-9, 1-16, 1-17, 1-21, 2-1 and 3-4, 14 parts of polyoxyethylene styrylphenyl ether, 6 parts of calcium dodecylbenzene sulfonate, 35 parts of xylene and 35 parts cyclohexanone are mixed well to obtain emulsifiable concentrates for each compound.

Formulation Example 3

Two (2) parts each of the present invention compound 1-1, 1-2, 1-9, 1-16, 1-17, 1-21, 2-1 and 3-4, 2 parts of synthetic hydrated silicon oxide, 2 parts of calcium ligninsulfonate, 30 parts of bentonite and 64 parts of kaolin clay are pulverized and mixed well. After the addition of water, the obtained mixture is kneaded, granulated, and then dried to obtain granules for each compound.

Formulation Example 4

Twenty-five (25) parts each of the present compound invention 1-1, 1-2, 1-9, 1-16, 1-17, 1-21, 2-1 and 3-4, 50 parts of 10% aqueous solution of polyvinyl alcohol and 25 parts of water are mixed and wet-pulverized until the average diameter becomes 5 µm or less to obtain flowables for each compound.

Formulation Example 5

Into 40 parts each of 10% aqueous solution of polyvinyl alcohol, 5 parts each of the present invention compounds 1-1, 1-2, 1-9, 1-16, 1-17, 1-21, 2-1 and 3-4 is added. Each obtained mixture is emulsified and dispersed with a homogenizer until the average diameter becomes 10 µm or less, and incorporated with 55 parts of water to obtain concentrated emulsion for each compound.

Hereinafter, the following test examples are provided, in order to evidence that the present invention compounds are effective as the active ingredient of a herbicide.

Test Example 1 Foliage Treatment Test for Upland Field

Cylindrical plastic pots each having a diameter of 10 cm and a depth of 10 cm were filled with soil and then seeded with ivyleaf morningglory (*Ipomoea hederacea*) and velvetleaf (*Abutilon theophrasti*). These test plants were grown in a greenhouse for 14 days. Afterwards, the present invention compound 1-1 was formulated into an emulsifiable concentrate according to Formulation Example 2 and then diluted to the prescribed amount with water containing a spreading agent, and the dilution was uniformly sprayed over the foliage of the test plants with a sprayer at a rate of 1000 liters per hectare After the application, the test plants were grown in the greenhouse for 8 days, and the herbicidal activity was examined. As a result, it was determined that the growth of ivyleaf morningglory and velvetleaf was completely controlled when compound 1-1 was applied at the dosage of 500 g/ha.

Test Example 2 Soil Treatment Test for Upland Field

Cylindrical plastic pots each having a diameter of 10 cm and a depth of 10 cm were filled with soil and then seeded with ivyleaf morningglory (*Ipomoea hederacea*). The present invention compound 1-1 was formulated into an emulsifiable concentrate according to Formulation Example 2 and then diluted to the prescribed amount with water and the dilution was uniformly sprayed over the surface of the soil with a sprayer at a rate of 1000 liters per hectare. After the application, the test plants were grown in the greenhouse for 9 days, and the herbicidal activity was examined. It was determined that compound 1 - 1 completely controlled the emergence of ivyleaf morningglory when applied at the dosage of 2000 g/ha.

Test Example 3 Flooding Treatment Test for Paddy Field

Cylindrical plastic pots each having a diameter of 9 cm and a depth of 11 cm were filled with soil and then seeded with barnyardgrass (*Echinochloa oryzicola*). After flooding the said pot until a paddy-field condition was obtained, the test plant was grown in a greenhouse. Twelve (12) days later, the present invention compound 1-1, 2-1 and 3-4,were formulated into emulsifiable concentrates according to Formulation Example 2, diluted to the prescribed amount with water, and were then treated onto the surface of the water at a rate of 50L per are. After the application, the test plants were grown in the greenhouse for 9 days, and then the herbicidal activity was examined. It was determined that barnyard grass was completely controlled when compound 1-1, 2-1 and 3-4 were applied at the dosage of 500 g/ha, respectively.

Test Example 4 Foliage Treatment Test for Upland Field

Cylindrical plastic pots each having a diameter of 10 cm and a depth of 10 cm were filled with soil and then seeded with and velvetleaf (*Abutilon theophrasti*). The test plants were grown in a greenhouse for 14 days. Afterwards, each of the present invention compound 1-1, 1-2, 1-9, 1-16, 1-17, 1-21, 1-31, 2-1 and 3-4 was formulated into an emulsifiable concentrate according to Formulation Example 2 and then diluted to the prescribed amount with water containing a spreading agent, and the dilution was uniformly sprayed over the foliage of the test plants with a sprayer at a rate of 1000 liters per hectare After the application, the test plants were grown in the greenhouse for 16 days, and the herbicidal activity was examined. As a result, it was determined that the growth of velvetleaf was completely controlled when compound 1-1, 1-2, 1-9, 1-16, 1-17, 1-21, 1-31, 2-1 and 3-4 were applied at the dosage of 2,000 g/ha, respectively.

Test Example 5 Soil Treatment Test for Upland Field

Cylindrical plastic pots each having a diameter of 10 cm and a depth of 10 cm were filled with soil and then seeded with ivyleaf morningglory (*Ipomoea hederacea*). Each of the present invention compound 1-16 and 1-21 was formulated into an emulsifiable concentrate according to Formulation Example 2 and then diluted to the prescribed amount with water and the dilution was uniformly sprayed over the surface of the soil with a sprayer at a rate of 1000 liters per hectare. After the application, the test plants were grown in the greenhouse for 19 days, and the herbicidal activity was examined. Compounds 1-16 and 1-21 completely controlled the emergence of ivyleaf morningglory, respectively when applied at the dosage of 2000 g/ha.

Test Example 6 Flooding Treatment Test for Paddy Field

Cylindrical plastic pots each having a diameter of 9 cm and a depth of 11 cm were filled with soil and then seeded with barnyardgrass (*Echinochloa oryzicola*). After flooding the said pot until a paddy-field condition was obtained, the test plant was grown in a greenhouse. Twelve (12) days later, the present invention compounds 1-1, 1-16, 1-17, 1-21, 1-31 and 2-1 were formulated into emulsifiable concentrates according to Formulation Example 2, diluted to the prescribed amount with water, and were then treated onto the surface of the water at a rate of 50L per are. After the application, the test plants were grown in the greenhouse for 19 days, and then the herbicidal activity was examined. It was determined that barnyard grass was completely controlled when compounds 1-1, 1-16, 1-17, 1-21, 1-31 and 2-1 were applied at the dosage of 1000 g/ha, respectively.

Effect of Invention

By utilizing the present invention compound, an excellent herbicidal efficacy can be obtained.

What is claimed is:

1. A pyridazinone derivative encompassed by the following formula:

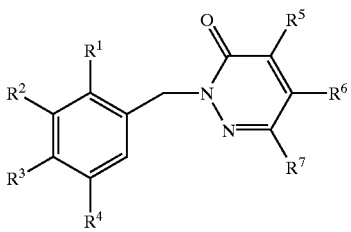

wherein, $R^1$ represents hydrogen, halogen, $C_1$–$C_3$ alkyl or $C_1$–$C_3$ haloalkyl;

$R^2$ represents hydrogen, halogen, $C_1$–$C_6$ alkyl, $C_1$–$C_6$ haloalkyl, $OR^8$, $SR^9$, $NHR^{10}$, $COOR^{11}$, $COR^{12}$, $SO_2R^{13}$, $NO_2$ or CN;

$R^3$ represents hydrogen, halogen, $C_1$–$C_6$ alkyl, $C_1$–$C_6$ haloalkyl, $C_1$–$C_3$ alkoxy $C_1$–$C_3$ alkyl, $OR^8$, $SR^9$, $NHR^{10}$, $COOR^{11}$, $COR^{12}$, $SO_2R^{13}$, $C(R^{121})=C(R^{14})(R^{15})$, $NO_2$ or CN;

$R^4$ represents hydrogen, halogen, $C_1$–$C_6$ alkyl, $C_1$–$C_6$ haloalkyl, $C_1$–$C_3$ alkoxy $C_1$–$C_3$ alkyl, $OR^8$, $SR^9$, $NHR^{10}$, $COOR^{11}$, $COR^{12}$, $SO_2R^{13}$, $C(R^{121})=C(R^{14})(R^{15})$, $C(R^{16})=NOR^{17}$, $NO_2$ or CN;

$R^5$ represents hydrogen, halogen or $C_1$–$C_3$ alkyl;

$R^6$ represents $C_1$–$C_3$ alkyl or $C_1$–$C_3$ haloalkyl;

$R^7$ represents hydrogen, halogen, or $C_1$–$C_3$ alkyl; and in which;

$R^8$ represents hydrogen, a $C_1$–$C_{10}$ alkyl, $C_1$–$C_{10}$ haloalkyl, $C_3$–$C_8$ alkenyl, $C_3$–$C_8$ haloalkenyl, $C_3$–$C_8$ alkynyl, $C_3$–$C_8$ haloalkynyl, $C_3$–$C_{10}$ cycloalkyl, $C_3$–$C_{10}$ cyclohaloalkyl, $C_3$–$C_{10}$ cycloalkenyl, $C_3$–$C_{10}$ cyclohaloalkenyl, $C_3$–$C_{10}$ cycloalkyl $C_1$–$C_3$ alkyl, $C_3$–$C_{10}$ cyclohaloalkyl $C_1$–$C_3$ alkyl, $C_3$–$C_{10}$ cycloalkenyl $C_1$–$C_3$ alkyl, $C_3$–$C_{10}$ cyclohaloalkenyl $C_1$–$C_3$ alkyl, $C_1$–$C_5$ alkylcarbonyl, $C_1$–$C_5$ haloalkylcarbonyl, $C_3$–$C_6$ cycloalkylcarbonyl, $C_3$–$C_6$ cyclohaloalkylcarbonyl, $C_1$–$C_6$ alkylcarbonyl $C_1$–$C_6$ alkyl, $C_1$–$C_6$ haloalkylcarbonyl $C_1$–$C_6$ alkyl, $C_1$–$C_6$ alkoxycarbonyl, $C_1$–$C_6$ haloalkoxycarbonyl, $C_3$–$C_{10}$ cycloalkoxycarbonyl, $C_3$–$C_{10}$ cyclohaloalkoxycarbonyl, $C_1$–$C_{10}$ alkoxycarbonyl $C_1$–$C_5$ alkyl, $C_1$–$C_{10}$ haloalkoxycarbonyl $C_1$–$C_5$ alkyl, $C_3$–$C_{10}$ cycloalkoxycarbonyl $C_1$–$C_5$ alkyl, $C_3$–$C_{10}$ cyclohaloalkoxycarbonyl $C_1$–$C_5$ alkyl, $C_1$–$C_6$ alkoxy $C_1$–$C_6$ alkyl, $C_1$–$C_6$ haloalkoxy $C_1$–$C_6$ alkyl, $C_1$–$C_6$ alkylthio $C_1$–$C_6$ alkyl, $C_1$–$C_6$ haloalkylthio $C_1$–$C_6$ alkyl, cyano $C_1$–$C_4$ alkyl, phenyl that may have a substituent or substituents, phenyl $C_1$–$C_3$ alkyl that may have a substituent or substituents, phenylcarbonyl that may have a substituent or substituents, $SO_2R^{20}$, $CH_2C(=O)CO_2R^{41}$, $CH(CH_3)C(=O)CO_2R^{41}$, $CH_2C(=NOR^{42})CO_2R^{41}$ or $CH(CH_3)C(=NOR^{42})CO_2R^{41}$;

$R^9$ represents hydrogen, $C_1$–$C_{10}$ alkyl, $C_1$–$C_{10}$ haloalkyl, $C_3$–$C_8$ alkenyl, $C_3$–$C_8$ haloalkenyl, $C_3$–$C_8$ alkynyl, $C_3$–$C_8$ haloalkynyl, $C_3$–$C_{10}$ cycloalkyl, $C_3$–$C_{10}$ cyclohaloalkyl, $C_3$–$C_{10}$ cycloalkenyl, $C_3$–$C_{10}$ cyclohaloalkenyl, $C_3$–$C_{10}$ cycloalkyl $C_1$–$C_3$ alkyl, $C_3$–$C_{10}$ cyclohaloalkyl $C_1$–$C_3$ alkyl, $C_3$–$C_{10}$ cycloalkenyl $C_1$–$C_3$ alkyl, $C_3$–$C_{10}$ cyclohaloalkenyl $C_1$–$C_3$ alkyl, $C_1$–$C_5$ alkylcarbonyl, $C_1$–$C_5$ haloalkylcarbonyl, $C_3$–$C_6$ cycloalkylcarbonyl, $C_3$–$C_6$ cyclohaloalkylcarbonyl, $C_1$–$C_6$ alkylcarbonyl $C_1$–$C_6$ alkyl, $C_1$–$C_6$ haloalkylcarbonyl $C_1$–$C_6$ alkyl, $C_1$–$C_6$ alkoxycarbonyl, $C_1$–$C_6$ haloalkoxycarbonyl, $C_3$–$C_{10}$ cycloalkoxycarbonyl, $C_3$–$C_{10}$ cyclohaloalkoxycarbonyl, $C_1$–$C_{10}$ alkoxycarbonyl $C_1$–$C_5$ alkyl, $C_1$–$C_{10}$ haloalkoxycarbonyl $C_1$–$C_5$ alkyl, $C_3$–$C_{10}$ cycloalkoxycarbonyl $C_1$–$C_5$ alkyl, $C_3$–$C_{10}$ cyclohaloalkoxycarbonyl $C_1$–$C_5$ alkyl, $C_1$–$C_6$ alkoxy $C_1$–$C_6$ alkyl, $C_1$–$C_6$ haloalkoxy $C_1$–$C_6$ alkyl, $C_1$–$C_6$ alkylthio $C_1$–$C_6$ alkyl, $C_1$–$C_6$ haloalkylthio $C_1$–$C_6$ alkyl, cyano $C_1$–$C_4$ alkyl, phenyl that may have a substituent or substituents, phenyl $C_1$–$C_3$ alkyl that may have a substituent or substituents, phenylcarbonyl that may have a substituent or substituents, $CH_2C(=O)CO_2R^{41}$, $CH(CH_3)C(=O)CO_2R^{41}$, $CH_2C(=NOR^{42})CO_2R^{41}$ or $CH(CH_3)C(=NOR^{42})CO_2R^{41}$;

$R^{10}$ represents hydrogen, $C_1$–$C_{10}$ alkyl, $C_1$–$C_{10}$ haloalkyl, $C_3$–$C_8$ alkenyl, $C_3$–$C_8$ haloalkenyl, $C_3$–$C_8$ alkynyl, $C_3$–$C_8$ haloalkynyl, $C_3$–$C_{10}$ cycloalkyl, $C_3$–$C_{10}$ cyclohaloalkyl, $C_3$–$C_{10}$ cycloalkenyl, $C_3$–$C_{10}$ cyclohaloalkenyl, $C_3$–$C_{10}$ cycloalkyl $C_1$–$C_3$ alkyl, $C_3$–$C_{10}$ cyclohaloalkyl $C_1$–$C_3$ alkyl, $C_3$–$C_{10}$ cycloalkenyl $C_1$–$C_3$ alkyl, $C_3$–$C_{10}$ cyclohaloalkenyl $C_1$–$C_3$ alkyl, $C_1$–$C_5$ alkylcarbonyl, $C_1$–$C_5$ haloalkylcarbonyl, $C_3$–$C_6$ cycloalkylcarbonyl, $C_3$–$C_6$ cyclohaloalkylcarbonyl, $C_1$–$C_6$ alkylcarbonyl $C_1$–$C_6$ alkyl, $C_1$–$C_6$ haloalkylcarbonyl $C_1$–$C_6$ alkyl, $C_1$–$C_6$ alkoxycarbonyl $C_1$–$C_6$ haloalkoxycarbonyl, $C_3$–$C_{10}$ cycloalkoxycarbonyl, $C_3$–$C_{10}$ cyclohaloalkoxycarbonyl, $C_1$–$C_{10}$ alkoxycarbonyl $C_1$–$C_5$ alkyl, $C_1$–$C_{10}$ haloalkoxycarbonyl $C_1$–$C_5$ alkyl, $C_3$–$C_{10}$ cycloalkoxycarbonyl $C_1$–$C_5$ alkyl, $C_3$–$C_{10}$ cyclohaloalkoxycarbonyl $C_1$–$C_5$ alkyl, $C_1$–$C_6$ alkoxy $C_1$–$C_6$ alkyl, $C_1$–$C_6$ haloalkoxy $C_1$–$C_6$ alkyl, $C_1$–$C_6$ alkylthio $C_1$–$C_6$ alkyl, $C_1$–$C_6$ haloalkylthio $C_1$–$C_6$ alkyl, cyano $C_1$–$C_4$ alkyl, phenyl that may have a substituent or substituents, phenyl $C_1$–$C_3$ alkyl that may have a substituent or substituents, phenylcarbonyl that may have a substituent or substituents, $SR^{18}$, $SOR^{19}$, $SO_2R^{20}$, $CH_2C(=O)CO_2R^{41}$, $CH(CH_3)C(=O)CO_2R^{41}$, $CH_2C(=NOR^{42})CO_2R^{41}$ or $CH(CH_3)C(=NOR^{42})CO_2R^{41}$;

$R^{11}$ represents hydrogen, $C_1$–$C_{10}$ alkyl, $C_1$–$C_{10}$ haloalkyl, $C_3$–$C_{10}$ alkenyl, $C_3$–$C_{10}$ haloalkenyl, $C_3$–$C_{10}$ alkynyl, $C_3$–$C_{10}$ haloalkynyl, $C_3$–$C_8$ cycloalkyl, $C_3$–$C_8$ cyclohaloalkyl, $N(R^{21})(R^{22})$, $N=C(R^{21})(R^{22})$, $C_1$–$C_5$ alkoxycarbonyl $C_1$–$C_3$ alkyl or $C_1$–$C_5$ haloalkoxycarbonyl $C_1$–$C_3$ alkyl;

$R^{12}$ represents hydrogen, chlorine, $C_1$–$C_5$ alkyl, $C_1$–$C_5$ haloalkyl, $C_3$–$C_6$ cycloalkyl, $C_3$–$C_6$ cyclohaloalkyl or $N(R^{23})(R^{24})$;

$R^{13}$ represents chlorine, $C_1$–$C_{10}$ alkyl, $C_1$–$C_{10}$ haloalkyl, $N(R^{25})(R^{26})$ or $OR^{27}$;

$R^{14}$ represents hydrogen, halogen or $C_1$–$C_3$ alkyl;

$R^{15}$ represents hydrogen, $COOR^{28}$, cyano or $C_1$–$C_5$ alkyl;

$R^{16}$ represents hydrogen, $C_1$–$C_4$ alkyl, $C_1$–$C_4$ haloalkyl, $C_3$–$C_5$ cycloalkyl or $C_3$–$C_5$ cyclohaloalkyl;

$R^{17}$ represents hydrogen, $C_1$–$C_{10}$ alkyl, $C_1$–$C_{10}$ haloalkyl, $C_3$–$C_6$ cycloalkyl, $C_3$–$C_6$ cyclohaloalkyl, $C_3$–$C_{10}$ cycloalkyl $C_1$–$C_3$ alkyl, $C_3$–$C_{10}$ cyclohaloalkyl $C_1$–$C_3$ alkyl, $C_3$–$C_5$ alkenyl, $C_3$–$C_5$ haloalkenyl, $C_3$–$C_5$ alkynyl, $C_3$–$C_5$ haloalkynyl, $C_1$–$C_5$ alkoxycarbonyl $C_1$–$C_3$ alkyl, $C_1$–$C_5$ haloalkoxycarbonyl $C_1$–$C_3$ alkyl, phenyl that may have a substituent or substituents or phenyl $C_1$–$C_3$ alkyl that may have a substituent or substituents;

$R^{18}$ represents $C_1$–$C_{10}$ alkyl, $C_1$–$C_{10}$ haloalkyl or phenyl that may have a substituent or substituents;

$R^{19}$ represents $C_1$–$C_{10}$ alkyl, $C_1$–$C_{10}$ haloalkyl, $C_3$–$C_8$ cycloalkyl, $C_3$–$C_8$ cyclohaloalkyl or phenyl that may have a substituent or substituents;

$R^{20}$ represents $C_1$–$C_{10}$ alkyl, $C_1$–$C_{10}$ haloalkyl, $C_3$–$C_8$ cycloalkyl, $C_3$–$C_8$ cyclohaloalkyl or phenyl that may have a substituent or substituents;

$R^{21}$ represents hydrogen or $C_1$–$C_5$ alkyl;

$R^{22}$ represents hydrogen, $C_1$–$C_5$ alkyl, $C_1$–$C_8$ haloalkyl or phenyl that may have a substituent or substituents;

$R^{23}$ represents hydrogen, $C_1$–$C_{10}$ alkyl, $C_1$–$C_{10}$ haloalkyl, $C_3$–$C_{10}$ cycloalkyl, $C_3$–$C_{10}$ cyclohaloalkyl or phenyl that may have a substituent or substituents;

$R^{24}$ represents hydrogen, $C_1$–$C_{10}$ alkyl or $C_1$–$C_{10}$ haloalkyl;

$R^{25}$ represents hydrogen, $C_1$–$C_5$ alkyl or $C_1$–$C_5$ haloalkyl;

$R^{26}$ represents hydrogen, $C_1$–$C_{10}$ alkyl or $C_1$–$C_{10}$ haloalkyl;

$R^{27}$ represents hydrogen, $C_1$–$C_{10}$ alkyl;

$R^{28}$ represents hydrogen, $C_1$–$C_{10}$ alkyl, $C_1$–$C_{10}$ haloalkyl, $C_3$–$C_{10}$ cycloalkyl, $C_3$–$C_{10}$ cyclohaloalkyl or phenyl that may have a substituent or substituents;

$R^{41}$ represents hydrogen, $C_1$–$C_6$ alkyl, $C_1$–$C_6$ haloalkyl, $C_3$–$C_8$ alkenyl and $C_3$–$C_8$ alkynyl, $R^{42}$ represents hydrogen, $C_1$–$C_6$ alkyl, $C_1$–$C_6$ haloalkyl, $C_3$–$C_8$ alkenyl and $C_3$–$C_8$ alkynyl, and $R^{121}$ represents hydrogen, chlorine $C_1$–$C_5$ alkyl, $C_1$–$C_5$ haloalkyl, $C_3$–$C_6$ cycloalkyl or $C_3$–$C_6$ cyclohaloalkyl.

2. The pyridazinone derivative recited in claim 1, wherein $R^1$ is hydrogen or halogen.

3. The pyridazinone derivative recited in claim 1, wherein $R^2$ is hydrogen or halogen.

4. The pyridazinone derivative recited in claim 1, wherein $R^1$ and $R^2$ are halogen.

5. The pyridazinone derivative recited in claim 1, wherein $R^5$ is hydrogen or $C_1$–$C_3$ alkyl.

6. The pyridazinone derivative recited in claim 1, wherein $R^7$ is hydrogen or $C_1$–$C_3$ alkyl.

7. The pyridazinone derivative recited in claim 1, wherein $R^6$ is $C_1$–$C_3$ haloalkyl.

8. The pyridazinone derivative recited in claim 1, wherein $R^6$ is trifluoromethyl.

9. The pyridazinone derivative recited in claim 3 wherein $R^1$ and $R^2$ are chlorine and $R^6$ is trifluoromethyl.

10. A herbicide comprising the pyridazinone derivative recited in claim 1 as an active ingredient and a herbicidally acceptable carrier therefor.

11. A method for controlling weeds which comprises applying an effective amount of a pyridazinone derivative as recited in claim 1 to weeds or a locus in which weeds grow or will grow.

* * * * *